US012778886B2

(12) United States Patent
Manus et al.

(10) Patent No.: US 12,778,886 B2
(45) Date of Patent: Nov. 3, 2026

(54) ORAL HYDROGEL COMPOSITIONS AND USES

(71) Applicant: Colgate-Palmolive Company, New York, NY (US)

(72) Inventors: Lisa Manus, Lawrenceville, NJ (US); Joseph Steele, Plainfield, NJ (US); Guillaume Picquet, Somerset, NJ (US); Christine Padula, Parsippany, NJ (US); Dandan Chen, Bridgewater, NJ (US); Betty Won, Princeton Junction, NJ (US); Andrei Potanin, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 625 days.

(21) Appl. No.: 18/251,428

(22) PCT Filed: Nov. 3, 2021

(86) PCT No.: PCT/US2021/057861
§ 371 (c)(1),
(2) Date: May 2, 2023

(87) PCT Pub. No.: WO2022/098730
PCT Pub. Date: May 12, 2022

(65) Prior Publication Data

US 2024/0024233 A1 Jan. 25, 2024

Related U.S. Application Data

(60) Provisional application No. 63/109,169, filed on Nov. 3, 2020.

(51) Int. Cl.

| | |
|---|---|
| ***A61K 9/06*** | (2006.01) |
| ***A61K 31/155*** | (2006.01) |
| ***A61K 47/10*** | (2017.01) |
| ***A61K 47/32*** | (2006.01) |
| ***A61K 47/36*** | (2006.01) |
| ***A61P 1/02*** | (2006.01) |

(52) U.S. Cl.
CPC .............. *A61K 9/06* (2013.01); *A61K 31/155* (2013.01); *A61K 47/10* (2013.01); *A61K 47/32* (2013.01); *A61K 47/36* (2013.01); *A61P 1/02* (2018.01)

(58) Field of Classification Search
None
See application file for complete search history.

(56) References Cited

U.S. PATENT DOCUMENTS

| | | | |
|---|---|---|---|
| 7,339,013 | B2 | 3/2008 | Pagnoux et al. |
| 2014/0301957 | A1 | 10/2014 | Mchale et al. |
| 2020/0054667 | A1 | 2/2020 | Mevorat Kaplan et al. |
| 2024/0024233 | A1 | 1/2024 | Manus et al. |

FOREIGN PATENT DOCUMENTS

| | | | | |
|---|---|---|---|---|
| FR | 3094222 | | 10/2020 | |
| GB | 2569560 | | 6/2019 | |
| GB | 2569560 A | * | 6/2019 | ............. A61Q 19/04 |
| WO | 2018/158763 | | 9/2018 | |
| WO | 2018/158764 | | 9/2018 | |
| WO | 2020/211859 | | 10/2020 | |
| WO | WO-2020211859 A1 | * | 10/2020 | ........... A61K 9/0024 |
| WO | 2022/098730 | | 5/2022 | |

OTHER PUBLICATIONS

Boonlai, Wannisa, et al., "Thermosensitive Poloxamer 407/ Poly(Acrylic Acid) Hydrogels with Potential Application as Injectable Drug Delivery System," AAPS PharmSciTech, 19(5):2103-2117 (2018).
H G Wisniewski, et al., "TNF/IL-1-inducible protein TSG-6 potentiates plasmin inhibition by inter-alpha-inhibitor and exerts a strong anti-inflammatory effect in vivo," J. Immun., 156(4):1609-1615 (1996).
Hansen, Irene M., et al., "Hyaluronic Acid Molecular Weight-Dependent Modulation of Mucin Nanostructure for Potential Mucosal Therapeutic Applications," Molecular Pharmaceutics, 14(7):2359-2367 (2017).
International Search Report and the Written Opinion of the International Searching Authority issued in International Application PCT/US2021/057861 mailed Feb. 24, 2022.
Jung, Young-Seok, et al., "Thermo-sensitive injectable hydrogel based on the physical mixing of hyaluronic acid and Pluronic F-127 for sustained NSAID delivery," Carbohydrate Polymers, 156:403-408 (2017).
Madsen, Flemming, et al., "A rheological assessment of the nature of interactions between mucoadhesive polymers and a homogenised mucus gel," Biomaterials 19, 1083-1092 (1998).
Slevin, Mark, et al., "Angiogenic Oligosaccharides of Hyaluronan Induce Multiple Signaling Pathways Affecting Vascular Endothelial Cell Mitogenic and Wound Healing Responses," J. Biol. Chem., 277:41046-41059 (2002).
International Search Report and the Written Opinion of the International Searching Authority issued in International Application PCT/US2025/049568 mailed Feb. 10, 2026.

* cited by examiner

*Primary Examiner* — Melissa S Mercier

(57) ABSTRACT

The present invention relates to oral hydrogel compositions, more particularly to thermosensitive gel compositions, which undergo a sol-gel transition in the oral cavity, and which optionally comprise therapeutic actives for sustained release.

17 Claims, No Drawings

ORAL HYDROGEL COMPOSITIONS AND USES

This application is an international application which claims priority to, and the benefit of, U.S. Provisional Application No. 63/109,169, filed on Nov. 3, 2020, the contents of which are hereby incorporated by reference in its entirety.

The present invention relates to oral hydrogel compositions, more particularly to thermosensitive gel compositions, which interact with mucin and undergo a sol-gel transition in the oral cavity, and which optionally comprise therapeutic actives for sustained release.

BACKGROUND

The oral cavity is subject to numerous conditions, including periodontal disease (including gingivitis and periodontitis), dental caries, dental hypersensitivity, halitosis, and oral infections (e.g., fungal or bacterial infections of the oral mucosa).

Dental erosion involves demineralization and damage to the tooth structure due to acid attack from nonbacterial sources. Erosion is found initially in the enamel and, if unchecked, may proceed to the underlying dentin. Generally, saliva has a pH between 7.2 to 7.4. When the pH is lowered and the concentration of hydrogen ions becomes relatively high, the tooth enamel can become microscopically etched, resulting in a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold), osmotic, tactile, or a combination of thermal, osmotic and tactile, stimulation of the exposed dentin. Exposure of the dentine, which is generally due to recession of the gums, or loss of enamel, frequently leads to hypersensitivity.

Oral cavity bacteria are the primary cause of dental ailments, including caries, gingivitis, periodontitis, and halitosis. Bacteria associated with dental plaque convert sugar to glucans, which are insoluble polysaccharides that provide plaque with its cohesive properties. Anaerobic bacteria in plaque metabolize sugar to produce acids which dissolve tooth minerals, damaging the enamel and eventually forming dental caries.

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization are caused by acid produced from the bacterial degradation of fermentable sugar.

Periodontal diseases are common ailments which affect a high proportion of the population especially at advanced age. Gingivitis, often caused by inadequate oral hygiene, is the mildest form of a periodontal disease that causes the gingiva (or gums) to become red, swollen, and bleed easily. While gingivitis can be reversible with professional treatment and good oral home care, untreated gingivitis can advance to periodontitis. With time, plaque can spread and grow below the gum line. Toxins produced by the bacteria in plaque irritate the gums, and stimulate a chronic inflammatory response following which the tissues and bone supporting the teeth are broken down and destroyed. Consequently, gums separate from the teeth, forming pockets (spaces between the teeth and gums) that become infected. As the disease progresses, those pockets deepen and more gum tissue and bone are destroyed. Often, this destructive process has very mild symptoms. Eventually, teeth may become loose and might have to be removed. Periodontal diseases are more difficult to treat compared to caries due to the markedly different environments of the oral and periodontal cavities. For example, whereas the oral cavity is essentially an aerobic environment constantly perfused by saliva, the periodontal microenvironment is more anaerobic and perfused by a plasma filtrate known as the "crevicular fluid". The growth of microorganisms within the periodontal microenvironment may cause periodontal disease, and as the periodontal disease becomes more established, said microenvironment becomes more anaerobic and the flow of crevicular fluid increases.

Various antibacterial agents can retard the growth of bacteria and thus reduce the formation of biofilm on oral surfaces. In many cases, these antibacterial agents are cationic, for example quaternary ammonium surfactants such as cetyl pyridinium chloride (CPC), biguanides such as chlorhexidine, metal cations such as zinc or stannous ions, and guanidines such as arginine. Soluble zinc salts, such as zinc citrate, and stannous ion sources, such as stannous fluoride and stannous chloride, exhibit excellent clinical benefits, particularly in the reduction of gingivitis.

Hyaluronic acid (also called hyaluronan or hyaluronate) is an anionic, non-sulfated glycosaminoglycan (GAG) widely distributed throughout connective tissues of vertebrates, being the most abundant glycosaminoglycan of higher molecular weight in the extracellular matrix of soft periodontal tissues. Hyaluronan has been found to be effective in the treatment of inflammatory processes in medical fields such as orthopedics, dermatology and ophthalmology, and it has been further found to be anti-inflammatory and antibacterial in gingivitis and periodontitis therapy.

While medicated toothpastes and mouthwashes are commonly used, the effect is often transient as the active agent may quickly be washed out of the oral cavity by rinsing, eating or drinking, and/or effective concentrations of active agent may be rendered ineffective by rapid dilution by saliva. It is particularly difficult to deliver toothpastes and mouthwashes into the tight periodontal cavity, which lies between the teeth roots and the gum.

The use of oral gels is known, most commonly in the form of gels for tooth cleaning and tooth whitening. Common polymers found in such gels include poloxamers (polyethylene glycol-polypropylene glycol block copolymers), gums (e.g., carrageenan, xanthan, guar, karaya, gellan), polyacrylate polymers, vinyl polymers and copolymers (e.g., povidone, crospovidone), polyethylene glycols, polyethylene glycol/polypropylene glycol copolymers, polyvinyl alcohols, modified cellulose polymers (e.g., carboxymethyl cellulose, hydroxypropyl methyl cellulose), polyvinyl ethers, and methyl vinyl ether/maleic anhydride copolymers.

Poloxamers in particular have been widely used in the biomedical field due to their ability to undergo phase reverse thermal gelation. Their self-assembling process occurs through micellization, which is characterized by their critical micellization concentration and critical micellization temperature. These parameters, which depend on the specific poloxamer used, can be tailored to obtain materials with final properties suitable for a wide range of applications. However, one of the drawbacks associated with poloxamer gels for delivery applications is the lack of adhesiveness, which results in short residence times. Another drawback of poloxamers is their rapid dissolution in aqueous media. Blending of poloxamers with mucoadhesive polymers that are capable of forming entanglements or non-covalent bonds with the mucus covering epithelial tissues is therefore one of the approaches to improving adhesiveness and residence time.

Thus, there remains a need for effective delivery or oral care agents to the oral cavity, especially to the periodontal cavity, preferably long-term sustained delivery of such agents.

SUMMARY OF INVENTION

The present disclosure provides a liquid thermosensitive hydrogel comprising (a) a linear polyethylene glycol (PEG)/polypropylene glycol (PPG) triblock copolymer (e.g., poloxamer 407), (b) a linear PEG/PPG triblock copolymer and polypropylene glycol (PPG)-SMDI copolymer (e.g., Expert-Gel 312 or 412), and (c) an aqueous carrier or non-aqueous polyol carrier. In particular embodiments, the hydrogel further comprises one or more of (d) an polyethylene glycol (PEG) polymer, (e) a polyacrylic acid or polyacrylate polymer (e.g., acrylic acid homopolymer), (f) high-molecular weight hyaluronic acid or an alkali metal hyaluronate polymer (>100,000 Da), and (g) one or more active agents (e.g., antibacterial agents). Hydrogels according to the invention have the unique property at or about room temperature they are free-flowing liquids, but upon exposure to typical human oral cavity temperature or mucin proteins or oral mucosa to a high-viscosity mucoadhesive gel occurs (e.g., having a viscosity of at least 1000 mPa-s). In embodiments wherein the hydrogel comprises an active ingredient, said ingredient is preferably uniformly distributed throughout the hydrogel such that upon gelation and mucoadhesion in the oral cavity the gel will gradually release the active ingredient in a predictable sustained manner. Preferably, the viscosity of the liquid composition is low enough to permit easy administration via a syringe with narrow bore needle, such as would be necessary for injection into the periodontal space (viscosity of <1000 mPa-s). As used herein, the term "liquid thermosensitive hydrogel" means a material that is a liquid at ambient conditions and converts to a gel (hydrogel) upon exposure to elevated temperature.

In additional aspects, the present disclosure provides oral care compositions comprising said hydrogels, and methods for the use thereof.

DETAILED DESCRIPTION

The present disclosure provides liquid thermosensitive hydrogels which are formulated to provide instantaneous intraoral swelling and mucoadhesion through significant increases in viscosity (e.g., at least a 100-fold increase in viscosity). Without being bound by theory, it is believed that the rapid viscosity change is achieved through at least two mechanisms: (1) thermosensitive gelation of the linear and cross-linked poloxamer systems, and (2) rheological synergism via attractive forces between the polymers (e.g., polyacrylates) and the oligosaccharides of oral mucin proteins. Continuous flow of saliva and/or gingival crevicular fluid will degrade the structure of such gels over a period of time, which allows for the controlled release of the polymers in the gel and/or of active ingredients embedded within the polymer matrix.

Without being bound by theory, it is believed that the carboxyl and hydroxyl groups of the polyacid polymers form hydrogen bonds with the hydroxyl groups of the glycosylated oral mucins. This entanglement alters the pellicle microstructure and mesh size increasing the density of this natural layer. Furthermore, compaction provides a greater barrier against bacteria or can be used to further amplify and trap actives within the mucosa. Moreover, localization of these polymer matrices in contact with damaged tissue areas have the potential to act as an exogenous scaffold for cellular infiltration enhancing wound healing. The inclusion of high molecular weight hyaluronic acid (MW>100,000 Da, e.g., 200 kDa-1 MDa, or 250 to 350 kDa), such as neutralized sodium hyaluronate, in the composition may further promote healing and anti-inflammatory action. It is believed that hyaluronic acid competitively binds to lipopolysaccharide (LPS) receptors, attenuating downstream inflammatory cytokine production. Hyaluronic acid, a natural product produced during wound healing, can also promote cell migration thereby accelerating the rate of tissue repair.

A variety of active ingredients may be dissolved or suspended in the liquid hydrogels, causing the actives to be embedded in the resultant oral gels. Cations such as CPC and chlorhexidine may be used, providing antibacterial properties, preservation, resistance to bacterial invasion, and additional structure building of the gel via ionic interactions with the polyacrylates. Metal oxides such as zinc oxide, and metal phosphates such as hydroxyapatite, may be included, which provide opacification and bulk to the gel structure. Polyphenols and other hydrophobic actives, such as eugenol, curcumin, and salicylic acid, may be included as well. The amphiphilic nature of the polymers of the present compositions can be used to solubilize and sequester hydrophobic or water-sensitive actives (e.g., antibiotics, dyes, anti-inflammatories, peroxides) within the highly aqueous formulation.

Compositions according to the present disclosure may be formulated as, for example, mucoadhesive tablets, rapid melt tablets, films, porous wafers, gels, ointments, water-based pastes, anhydrous pastes, powders, patches, non-woven microfiber sheets, liquid band-aids, structured mouthwashes, mouthwashes, serums, sprays, wafers, mucoadhesive powders, and mucoadhesive coatings. In particular embodiments, the present disclosure provides a viscous gel which can be injected into the periodontal pocket or applied directly to an oral cavity wound, such as the dental socket after tooth extraction or to the damaged surface of a tooth. Without being bound by theory, it is believed that the complex cross-linked polymer network of the gel serves as a barrier to infection by physically preventing access of oral cavity (e.g., salivary) bacteria or fungi to the wound site. In some embodiments, the viscous gel also comprises antibacterial and/or antifungal ingredients, preservatives, or ingredients which promote wound-healing, and such ingredients act as part of the barrier as well as slowly releasing to the oral tissues as the gel matrix degrades over time. Such ingredients include, for example, hyaluronic acid (or its salts), chlorhexidine gluconate, cetylpyridinium chloride, and zinc salts (such as zinc oxide).

In a first aspect, the present disclosure provides a liquid thermosensitive hydrogel (Hydrogel 1) comprising (a) linear polyethylene glycol (PEG)/polypropylene glycol (PPG) triblock copolymer (e.g., poloxamer 407), (b) a linear PEG/PPG triblock copolymer and polypropylene glycol (PPG)-SMDI copolymer (e.g., ExpertGel 312 or 412), and (c) an aqueous carrier or non-aqueous polyol carrier. In particular embodiments, the present disclosure further provides:

1.1. Hydrogel 1, wherein the (a) PEG/PPG triblock copolymer has the structure HO—$[CH_2CH_2O]_a$[—CH $(CH_3)CH_2O—]_b[CH_2CH_2O]_a$—H, wherein a is an integer between 50 and 130, b is an integer between 30 and 80.

1.2. Hydrogel 1.1, wherein the (a) PEG/PPG triblock copolymer has said structure wherein a is an integer between 75 and 125 and b is an integer between 50 and 70, or wherein a is an integer between 85 and 115, and b is an integer between 55 and 65, or wherein a is an integer between 90 and 110 and b is an integer between 55 and 60, or wherein a is an integer between 95 and 105 and b is an integer between 55 and 57, or wherein a is an integer between 98 and 101, and b is about 56.

1.3. Hydrogel 1.1 or 1.2 wherein the (a) PEG/PPG triblock copolymer has a PPG core (i.e., $[—CH(CH_3)CH_2O—]_b$) molecular weight of about 2500 to 5000 Da, or about 3000 to 4500 Da, or about 3500 to 4100 Da, or about 3500 to 3700 Da, or about 3700 to 4100 Da, or about 3600 Da or about 4000 Da.

1.4. Any of Hydrogels 1.1-1.3, wherein the (a) PEG/PPG triblock copolymer has a polyethylene oxide content of about 60 to 80% by weight, e.g., about 70% by weight.

1.5. Any of Hydrogels 1.1-1.4, wherein the (a) PEG/PPG triblock copolymer has a molecular weight of 5000 to 25,000 Da, or about 7000 to 20,000 Da, or about 8000 to 16,000 Da, or about 9000 to 15,000 Da, or about 9840 to 14,600 Da.

1.6. Any of Hydrogels 1.1-1.5, wherein the (a) PEG/PPG triblock copolymer has an HLB (hydrophilic-lipophilic balance) value of 18-22.

1.7. Any of Hydrogels 1.1-1.6, wherein the (a) PEG/PPG triblock copolymer is Poloxamer 407.

1.8. Hydrogel 1, or any of 1.1.1-7, wherein the hydrogel comprises the (a) PEG/PPG triblock copolymer in an amount of 0.1 to 20 wt %, e.g., 1 to 10 wt %, or 2 to 8 wt %, or 3 to 7 wt %, or 4 to 6 wt %, or about 5 wt %.

1.9. Hydrogel 1, or any of 1.1-1.8, wherein the (b) linear PEG/PPG triblock copolymer and PPG-SMDI copolymer consists of linear PEG/PPG triblock copolymer portions, PPG portions and SMDI portions (e.g., poloxamer 338 or 407 portions, PPG-12 portions, and SMDI portions).

1.10. Hydrogel 1.9, wherein component (b) is a mixture of the linear PEG/PPG triblock copolymer and a copolymer of PPG and SMDI.

1.11. Hydrogel 1.9, wherein the component (b) is a linear PEG/PPG triblock copolymer covalently linked to a copolymer of PPG and SMDI (e.g., poloxamer 338 or 407 covalently linked to a PPG-12/SMDI copolymer).

1.12. Hydrogel 1.9, wherein the component (b) is a linear PEG/PPG triblock copolymer cross-linked with a copolymer of PPG and SMDI (e.g., poloxamer 338 or 407 cross-linked with a PPG-12/SMDI copolymer).

1.13. Hydrogel 1.9, wherein the PPG (e.g., PPG-12) is condensed with SMDI.

1.14. Hydrogel 1.9, wherein the linear PEG/PPG triblock copolymer is condensed with SMDI (e.g., poloxamer 338 or 407 condensed with SMDI).

1.15. Hydrogel 1.9, wherein the linear PEG/PPG triblock copolymer and the PPG are both condensed with SMDI (e.g., with condensation occurring between the SMDI and the hydroxy termini of the PEG/PPG triblock copolymer, e.g., poloxamer 338 or poloxamer 407, and/or the PPG, e.g., PPG-12).

1.16. Any of Hydrogels 1.9-1.12, wherein the PPG has an average n value (average number of moles of propylene oxide in the polymer) of 3 to 70.

1.17. Hydrogel 1.16, wherein the PPG has an average n value of 3 to 30, or 3 to 20, or 7 to 16, or 9 to 15, or about 12 (e.g., the PPG is PPG-12).

1.18. Any of Hydrogels 1.9-1.17, wherein the (b) component linear PEG/PPG triblock copolymer has the structure $HO—[CH_2CH_2O]_a[—CH(CH_3)CH_2O—]_b[CH_2CH_2O]_a$—H, wherein a is an integer between 100 and 200, b is an integer between 30 and 80.

1.19. Hydrogel 1.18, wherein the (b) component linear PEG/PPG triblock copolymer has said structure wherein a is an integer between 125 and 175 and b is an integer between 30 and 70, or wherein a is an integer between 135 and 165, and b is an integer between 40 and 60, or wherein a is an integer between 140 and 150 and b is an integer between 40 and 50, or wherein a is about 141, and b is about 44.

1.20. Hydrogel 1.18 or 1.19 wherein the (b) component linear PEG/PPG triblock copolymer has a PPG core molecular weight of about 2000 to 5000 Da, or about 2500 to 4000 Da, or about 3000 to 3500 Da, or about 3300 Da.

1.21. Any of Hydrogels 1.18-1.20, wherein the (b) component linear PEG/PPG triblock copolymer has a polyethylene oxide content of about 70 to 90% by weight, e.g., about 80% by weight.

1.22. Any of Hydrogels 1.18-1.21, wherein the (b) component linear PEG/PPG triblock copolymer is poloxamer 338.

1.23. Any of Hydrogels 1.9-1.17, wherein the (b) component linear PEG/PPG triblock copolymer has the structure $HO—[CH_2CH_2O]_a[—CH(CH_3)CH_2O—]_b[CH_2CH_2O]_a$—H, wherein a is an integer between 50 and 130, b is an integer between 30 and 80.

1.24. Hydrogel 1.23, wherein the (b) component linear PEG/PPG triblock copolymer has said structure wherein a is an integer between 75 and 125 and b is an integer between 50 and 70, or wherein a is an integer between 85 and 115, and b is an integer between 55 and 65, or wherein a is an integer between 90 and 110 and b is an integer between 55 and 60, or wherein a is an integer between 95 and 105 and b is an integer between 55 and 60, or wherein a is an integer between 98 and 101, and b is about 56.

1.25. Hydrogel 1.23 or 1.24 wherein the (b) component linear PEG/PPG triblock copolymer has a PPG core molecular weight of about 2500 to 5000 Da, or about 3000 to 4500 Da, or about 3500 to 4100 Da, or about 3500 to 3700 Da, or about 3700 to 4100 Da, or about 3600 Da or about 4000 Da.

1.26. Any of Hydrogels 1.23-1.25, wherein the (b) component linear PEG/PPG triblock copolymer has a polyethylene oxide content of about 60 to 80% by weight, e.g., about 70% by weight.

1.27. Any of Hydrogels 1.23-1.26, wherein the (b) component linear PEG/PPG triblock copolymer has a molecular weight of 5000 to 25,000 Da, or about 7000 to 20,000 Da, or about 8000 to 16,000 Da, or about 9000 to 15,000 Da, or about 9840 to 14,600 Da.

1.28. Any of Hydrogels 1.23-1.27, wherein the (b) component PEG/PPG triblock copolymer has an HLB (hydrophilic-lipophilic balance) value of 18-22

1.29. Any of Hydrogels 1.23-1.28, wherein the (b) component linear PEG/PPG triblock copolymer is poloxamer 407.

1.30. Any of Hydrogels 1.1-1.29, wherein component (b) is ExpertGel 412 (e.g., a poloxamer 407/PPG-12/SMDI copolymer).

1.31. Any of Hydrogels 1.1-1.29, wherein component (b) is ExpertGel 312 (e.g., a poloxamer 338/PPG-12/SMDI copolymer).

1.32. Any of Hydrogels 1.18-1.31, wherein the hydrogel comprises component (b) (e.g., ExpertGel 312 or ExpertGel 412) in an amount of 1 to 20 wt %, e.g., 5-15 wt % or 5-10 wt % or 8 to 12 wt % or about 10 wt %.

1.33. Hydrogel 1 or any of 1.1-1.32, wherein the carrier comprises water, ethanol, glycerol, propylene glycol, sorbitol, and xylitol, or mixtures thereof.

1.34. Hydrogel 1.33, wherein the carrier comprises water, ethanol, glycerol, propylene glycol, and mixtures thereof.

1.35. Hydrogel 1.34, wherein the carrier is water (e.g., without any polyol humectants).

1.36. Hydrogel 1.34, wherein the carrier is a non-aqueous polyol carrier (i.e., without added water, other than the intrinsic water content of any polyol carriers).

1.37. Hydrogel 1.36, wherein the hydrogel is formulated with water, but is freeze-dried to remove all or substantially all water from the hydrogel.

1.38. Hydrogel 1 or any of 1.1-1.36, wherein the hydrogel comprises the carrier (e.g., water or a water/polyol mixture) in an amount of 50 to 90 wt %, e.g., 60 to 90 wt %, or 70 to 90 wt %, or 80 to 90 wt %, or 50 to 70%, or 60 to 80 wt %, or 70 to 80 wt %, or 70 to 90 wt %.

1.39. Hydrogel 1 or any of 1.1-1.38, wherein the hydrogel further comprises one or more of (d) a polyethylene glycol (PEG) polymer, (e) a polyacrylic acid or polyacrylate polymer (e.g., acrylic acid homopolymer), (f) high-molecular weight hyaluronic acid or an alkali metal hyaluronate polymer (>100,000 Da), and (g) one or more active agents (e.g., antibacterial agents).

1.40. Any of Hydrogels 1.14-1.39, wherein the hydrogel further comprises a polyethylene glycol (PEG) polymer.

1.41. Hydrogel 1.40, wherein the PEG polymer has an average molecular weight of 400 to 20,000 (i.e., PEG-400 to PEG-20,000).

1.42. Hydrogel 1.41, wherein the PEG polymer has an average molecular weight of 2000 to 12,000 (e.g., PEG-2000 to PEG-12000).

1.43. Hydrogel 1.41, or 1.42, wherein the PEG polymer has an average molecular weight of 6000 to 10,000 Da (e.g., PEG-6000 to PEG-10000).

1.44. Any of Hydrogels 1.40-1.43, wherein the hydrogel comprises PEG-6000, PEG-8000, PEG-10000, or a combination thereof.

1.45. Any of Hydrogels 1.40-1.44, wherein the hydrogel comprises PEG polymer in an amount of 0.1 to 3 wt %, e.g., 0.1 to 2 wt %, or 0.1 to 1 wt %, or 0.1-0.5 wt %, or 0.5-1 wt %.

1.46. Hydrogel 1 or any of 1.1-1.45, wherein the hydrogel further comprises a polyacrylic acid or polyacrylate polymer (e.g., acrylic acid homopolymer), such a Carbomer homopolymer Type A.

1.47. Hydrogel 1.46, wherein the polyacrylic acid or polyacrylate polymer is a cross-linked polymer, e.g., cross-linked with allyl sucrose or allyl pentaerythritol.

1.48. Hydrogel 1.47, wherein the polyacrylic acid or polyacrylate polymer is a highly cross-linked polymer, e.g., having a viscosity of 29,000 to 40,000 mPa-s, such as Carbomer 974P NF.

1.49. Hydrogel 1.47, wherein the polyacrylic acid or polyacrylate polymer is a lightly cross-linked polymer, e.g., having a viscosity of 4,000 to 11,000 mPa-s, such as Carbomer 971P NF.

1.50. Any of Hydrogels 1.46-1.49, wherein the hydrogel comprises the polyacrylic acid or polyacrylate polymer in an amount of 0.05 to 5 wt %, e.g., 0.1 to 2 wt %, or 0.1 to 1 wt %, or 0.1 to 0.5 wt %, or about 0.3 wt %.

1.51. Hydrogel 1, or any of 1.1-1.50, wherein the hydrogel further comprises a high-molecular weight hyaluronic acid or an alkali metal hyaluronate polymer (>100,000 Da).

1.52. Hydrogel 1.51, wherein the hyaluronic acid or alkali metal hyaluronate polymer has an average molecular weight of 200,000 to 1,500,000 Da, e.g., 300,000 to 1,200,000 Da, or 300,000 to 700,000 Da, or 700,000 to 1,100,000 Da, or 300,000 to 450,000, or 350,000 to 600,000 Da, or 900,000 to 1,100,000 Da, or 250,000 to 700,000 Da, or 250,000 to 500,000 Da, or 250,000 to 350,000 Da, or about 290,000 Da, or about 315,000 Da, or about 370,000 Da, or about 480,000 Da, or about 1,000,000 Da.

1.53. Hydrogel 1.51 or 1.52, wherein the hyaluronic acid or alkali metal hyaluronate polymer is sodium hyaluronate polymer.

1.54. Any of Hydrogels 1.51-1.53, wherein the hydrogel comprises the hyaluronic acid or alkali metal hyaluronate polymer in an amount of 0.01 to 10 wt %, e.g., 0.01 to 5 wt %, 0.05 to 5 wt %, 0.1 to 2 wt %, or 0.1 to 1 wt %, or 0.3 to 0.5 wt %, or about 0.4 wt %; and optionally, wherein the weight ratio of the component (a) linear PEG/PPG triblock copolymer (e.g., poloxamer 407) to the hyaluronic acid or alkali metal hyaluronate polymer is 10:1 to 30:1, e.g., 10:1 to 25:1, or 10:1 to 20:1, or 10:1 to 15:1 or about 12.5:1.

1.55. Hydrogel 1, or any of 1.1-1.54, wherein the hydrogel further comprises one or more active agents (e.g., antibacterial agents or antifungal agents).

1.56. Hydrogel 1.55, wherein the active agent is selected from zinc salts, stannous salts, quaternary ammonium compounds, guanidines, amino acids, amino acid complexes, fluoride ion sources, tetrahydrocurcumin, vitamins, antibacterial agents, antifungal agents, anti-sensitivity agents, anti-inflammatory agents, anesthetic agents (e.g., local anesthetics), essential oils, and combinations thereof.

1.57. Hydrogel 1.56, wherein the active agent is selected from zinc oxide, zinc citrate, zinc sulfate, zinc chloride, zinc phosphate, zinc lactate, zinc pyrophosphate, zinc salicylate, zinc picolinate, stannous chloride, stannous fluoride, stannous pyrophosphate, cetylpyridinium chloride, benzalkonium chloride, chlorhexidine (e.g., chlorhexidine gluconate), arginine (e.g., arginine carbonate, arginine bicarbonate, arginine hydrochloride), lysine, histidine, zinc-bislysine-chloride complexes, zinc-bisarginine-chloride complexes, sodium fluoride, sodium monofluorophosphate, amine fluorides, tetrahydrocurcumin, eugenol, nicotinamide, riboflavin, sodium nitrate, potassium nitrate, strontium nitrate, eucalyptol, thymol, menthol, hydrogen peroxide, doxycycline, minocycline, ketoconazole, or combinations thereof.

1.58. Hydrogel 1.57, wherein the active agent is zinc oxide, cetylpyridinium chloride, chlorhexidine gluconate, eugenol, or a combination thereof.

1.59. Any of Hydrogels 1.56 to 1.58, wherein each active agent is present in an amount of 0.01 to 5 wt %, e.g., 0.05 to 2.5%, or 0.1 to 1%, or 0.05 to 0.5 wt %.

1.60. Hydrogel 1.58, wherein the hydrogel comprises zinc oxide in an amount of 0.1 to 1 wt %, e.g., about 0.5 wt %; and/or cetylpyridinium chloride in an amount of 0.01 to 0.2%, e.g., about 0.015% or about 0.075 wt %; and/or chlorhexidine gluconate in an amount of 0.1 to 5%, e.g., about 2.5% or about 5%; and/or eugenol in an amount of 0.1 to 0.5%, e.g., about 0.3%.

1.61. Hydrogel 1 or any of 1.1-1.60, wherein the hydrogel comprises (a) linear polyethylene glycol (PEG)/polypropylene glycol (PPG) triblock copolymer (e.g., poloxamer 407), (b) a linear PEG/PPG triblock copolymer and polypropylene glycol (PPG)-SMDI copolymer (e.g., ExpertGel 312 or 412), (c) an aqueous carrier or non-aqueous polyol carrier, (d) a polyacrylic acid or polyacrylate polymer (e.g., acrylic acid homopolymer), and (e) high-molecular weight hyaluronic acid or an alkali metal hyaluronate polymer (>100,000 Da); for example, wherein the hydrogel does not comprise polyethylene glycol polymers.

1.62. Hydrogel 1.61, wherein the hydrogel comprises (a) Poloxamer 407, (b) poloxamer 407 or 338 and PPG-12/SMDI copolymer, (c) water, (d) Carbomer 971P or 974P, and (e) sodium hyaluronate having a molecular weight of 350,000 to 600,000 Da, or 250,000 to 250,000 Da, wherein the poloxamer and PPG-12/SDMI copolymer of component (b) is ExpertGel 312 or ExpertGel 412.

1.63. Hydrogel 1.62, wherein the hydrogel comprises 1-10 wt % of the poloxamer 407, 0.1-0.5 wt % of the Carbomer 971P or 974P, 1-10 wt % of the ExpertGel 312 or ExpertGel 412, and 0.01 to 1 wt % of the sodium hyaluronate polymer, and 70-90 wt % water.

1.64. Hydrogel 1.62 or 1.63, wherein the weight ratio of poloxamer 407 to ExpertGel 312 or ExpertGel 412 is from 1:1.5 to 1:2.5, or about 1:2.

1.65. Hydrogel 1.62, 1.63, or 1.64, wherein the weight ratio of poloxamer 407 to Carbomer 971P or 974P is 15:1 to 20:1, or about 17:1.

1.66. Any of Hydrogels 1.62-1.65, wherein the weight ratio of poloxamer 407 to Carbomer 971P or 974P to ExpertGel 312 or ExpertGel 412 is (15-20):1:(30-40), optionally wherein the weight amount of poloxamer 407 is about 17:1:33.

1.67. Any of Hydrogels 1.62-1.66, wherein the hydrogel comprises 8-12 wt % poloxamer 407 (e.g., about 10 wt %), 0.2-0.4 wt % of the Carbomer 971P or 974P (e.g., about 0.3 wt %), 4-6 wt % of the ExpertGel 312 or ExpertGel 412 (e.g., about 5 wt %), and 0.3 to 0.7 wt % of the sodium hyaluronate polymer (e.g., about 0.4 wt %), and 80-90 wt % water (e.g., 80-85 wt %).

1.68. Any of Hydrogels 1.62-1.67, wherein the hydrogel further comprises zinc oxide in an amount of 0.1 to 1 wt % (e.g., about 0.5 wt %) and/or cetylpyridinium chloride in an amount of 0.01 to 0.2 wt % (e.g., about 0.015 wt % or 0.075 wt %) and/or chlorhexidine gluconate in an amount of 1 to 10 wt % (e.g., 2.5 or 5 wt %).

1.69. Hydrogel 1, or any of 1.1-1.68, further comprising one or more surfactants, e.g., anionic, cationic, nonionic, or zwitterionic surfactants, in a total amount of 0.1 to 5%.

1.70. Hydrogel 1.69, wherein the one or more surfactants are selected from cocamidopropyl betaine, sodium lauryl sulfate, sodium lauryl ether sulfate, ammonium lauryl sulfate, cocomonoethanolamide, cocodiethanolamide, laurylamidopropyl dimethylamine oxide, myristylamidopropyl dimethylamine oxide, decyl glucoside, sodium N-cocoyl-N-methyl taurate, sodium cocoyl isoethioniate, sodium dioctyl sulfosuccinate).

1.71. Hydrogel 1.70, wherein the one or more surfactants are present each in an amount of 0.1 to 5%, e.g., 0.5 to 2.5%, or 1 to 1.5%, or about 1.5%.

1.72. Hydrogel 1, or any of 1.1-1.71, further comprising one or more preservatives (e.g., benzyl alcohol), coloring agents, flavoring agents (e.g., eugenol), sweeteners, buffers (e.g., acids or bases, such as sodium carbonate or sodium bicarbonate), antioxidants (e.g., p-hydroxyacetophenone, ascorbic acid, beta-carotene, retinol, alpha-tocopherol, propyl gallate, tertiary butylhydroquinone, butylated hydroxyanisole, butylated hydroxytoluene), or other oral care ingredients, for example, each in an amount of less than 0.5 wt %, or less than 0.3 wt %, or less than 0.1 wt %, or less than 0.05 wt %.

1.73. Hydrogel 1, or any of 1.1-1.72, wherein the hydrogel has a pH of 5.5 to 9.5, e.g., 5.5-6.5, or 5.5-6.0, or 6.0-7.0, or 7.0-9.5, or 8.0-9.5, or 8.5-9.5, (e.g., 9.0).

1.74. Hydrogel 1, or any of 1.1-1.73, wherein the hydrogel is fluid at ambient temperature but transitions to a viscous gel in the oral cavity (e.g., in the periodontal cavity or oral mucosa).

1.75. Hydrogel 1.74, wherein the hydrogel has a viscosity (e.g., Brookfield viscosity) of less than 15,000 mPa-s, e.g., less 10,000 mPa-s, or less than 5,000 mPa-s, or less than 1000 mPa-s, or less than 500 mPa-s, or less than 200 mPa-s and at least 1 mPa-s, at a temperature below 30° C. (e.g., at 20-30° C. or at about 25° C.) and/or in the absence of mucin (e.g., outside of the oral cavity).

1.76. Hydrogel 1.74 or 1.75, wherein the hydrogel has a maximum instantaneous viscosity of less than 10,000 Pa-s, e.g., less 8,000 Pa-s, or less than 5,000 Pa-s, or less than 3000 Pa-s, or less than 2500 Pa-s, or less than 2000 Pa-s and at least 100 Pa-s, at a temperature below 30° C. (e.g., at 20-30° C. or at about 25° C.) and/or in the absence of mucin (e.g., outside of the oral cavity).

1.77. Hydrogel 1.74, 1.75 or 1.76, wherein the hydrogel has a G'/G" ratio below 3.0, e.g., below 2.0, or below 1.0, or below 0.75, or below 0.50, at a temperature below 30° C. (e.g., at 20-30° C. or at about 25° C.) and/or in the absence of mucin (e.g., outside of the oral cavity).

1.78. Hydrogel 1.74, 1.75, 1.76 or 1.77, wherein the hydrogel is triggered to transition to a viscous gel at a temperature above 30° C. and below 40° C., e.g., at a temperature of 35° C. to 39° C., or 36° C. to 38° C. (e.g., at about 37° C.) and/or at a pH of 6.5 or above (e.g., 7.0 or above), and/or wherein the hydrogel is triggered to transition to a viscous gel on exposure to oral mucin (e.g., oral human mucin).

1.79. Hydrogel 1.78, wherein the viscosity (e.g., Brookfield viscosity) of the resulting viscous gel is at least 1000 mPa-s and/or up to about 5,000,000 mPa-s, e.g., 2000 to 2,000,000 mPa-s, or 10,000 to 1,600,000 mPa-s, or 50,000 to 1,400,000 mPa-s, or 200,000 to 1,200,000 mPa-s, or about 1,000,000 mPa-s.

1.80. Hydrogel 1.78 or 1.79, wherein the maximum instantaneous viscosity of the resulting viscous gel is at least 9,000 Pa-s and/or up to about 50,000 Pa-s, e.g., 10,000 to 35,000 mPa-s, or 10,000 to 25,000 mPa-s, or 10,000 to 20,000 mPa-s, or 10,000 to 15,000 mPa-s.

1.81. Hydrogel 1.78, 1.79 or 1.80, wherein the G'/G" ratio of the resulting viscous gel is at least 1.0, e.g., 1.0 to 6.0, or 1.5 to 6.0, or 2.0 to 6.0, or 2.5 to 6.0, or 3.0 to 6.0, or 3.2 to 6.0, or 3.5 to 6.0, or 4.0 to 6.0.

1.82. Hydrogel 1.74-1.81, wherein the resulting viscous gel adheres to the mucous lining of the oral cavity (e.g., the periodontal cavity).

1.83. Hydrogel 1.74-1.82, wherein the resulting viscous gel interacts with mucin to strengthen adherence to the mucosal surface of the oral cavity (e.g., periodontal cavity or oral mucosa), such as due to rheological synergy with mucin.

1.84. Any of Hydrogels 1.74-1.83, wherein the resulting viscous gel slowly releases any active agent and/or any hyaluronic acid or alkali metal hyaluronate in a sustained manner (e.g., at a rate of 1-20% of the active agent content per day for a period of at least 1 day, such as over 1 to 30 days).

In another embodiment of the first aspect, the present disclosure provides a solid or semi-solid hydrogel (Hydrogel 1A) which is formulated according to any of Hydrogels 1 or 1.1-1.84 (those embodiments comprising water), followed by the further processing step of dehydrating or freeze-drying the Hydrogel to remove all or substantially all water from the composition to produce a solid or semi-solid pill, such as a tablet or wafer. Upon reconstituting with water (or saliva, such as in the oral cavity) Hydrogel 1A behaves as would be expected for Hydrogel 1 (or any of 1.1-1.84), by transitioning to a viscous gel (either passing through a fully liquid fluid phase, or by proceeding by way of a gel of low or medium viscosity which quickly transitions to a highly viscous gel).

In a second aspect, the present disclosure provides a solid or semi-solid non-aqueous or low-water thermosensitive hydrogel (Hydrogel 2) comprising (a) linear polyethylene glycol (PEG)/polypropylene glycol (PPG) triblock copolymer (poloxamer), and (b) a polyol carrier, wherein the water content is not more than 50% by weight. In particular embodiments, the present disclosure further provides:

2.1. Hydrogel 2, wherein the PEG/PPG triblock copolymer has the structure $HO—[CH_2CH_2O]_a[—CH(CH_3)CH_2O—]_b[CH_2CH_2O]_a—H$, wherein a is an integer between 50 and 130, b is an integer between 30 and 80.

2.2. Hydrogel 2.1, wherein the PEG/PPG triblock copolymer has said structure wherein a is an integer between 75 and 125 and b is an integer between 50 and 70, or wherein a is an integer between 85 and 115, and b is an integer between 55 and 65, or wherein a is an integer between 90 and 110 and b is an integer between 55 and 60, or wherein a is an integer between 95 and 105 and b is an integer between 55 and 57, or wherein a is an integer between 98 and 101, and b is about 56.

2.3. Hydrogel 2.1 or 2.2 wherein the PEG/PPG triblock copolymer has a PPG core molecular weight of about 2500 to 5000 Da, or about 3000 to 4500 Da, or about 3500 to 4100 Da, or about 3500 to 3700 Da, or about 3700 to 4100 Da, or about 3600 Da or about 4000 Da.

2.4. Any of Hydrogels 2.1-2.3, wherein the PEG/PPG triblock copolymer has a polyethylene oxide content of about 60 to 80% by weight, e.g., about 70% by weight.

2.5. Any of Hydrogels 2.1-2.4, wherein the (a) PEG/PPG triblock copolymer has a molecular weight of 5000 to 25,000 Da, or about 7000 to 20,000 Da, or about 8000 to 16,000 Da, or about 9000 to 15,000 Da, or about 9840 to 14,600 Da.

2.6. Any of Hydrogels 2.1-2.5, wherein the (a) PEG/PPG triblock copolymer has an HLB (hydrophilic-lipophilic balance) value of 18-22.

2.7. Any of Hydrogels 2.1-2.6, wherein the PEG/PPG triblock copolymer is Poloxamer 407.

2.8. Hydrogel 2, or any of 2.1.2-7, wherein the hydrogel comprises the PEG/PPG triblock copolymer in an amount of 0.1 to 20 wt %, e.g., 1 to 10 wt %, or 2 to 8 wt %, or 3 to 7 wt %, or 4 to 6 wt %, or about 5 wt %, or 10 to 30 wt %, or about 20 wt %.

2.9. Hydrogel 2 or any of 2.1-2.8, wherein the carrier is selected from water, ethanol, glycerol, propylene glycol, sorbitol, and xylitol, or mixtures thereof.

2.10. Hydrogel 2.9, wherein the carrier is selected from glycerol, sorbitol, propylene glycol, and mixtures thereof.

2.11. Hydrogel 2.10, wherein the carrier is propylene glycol or an ethanol/propylene glycol mixture or a sorbitol/glycerol mixture or sorbitol.

2.12. Hydrogel 2 or any of 2.1-2.11, wherein the hydrogel comprises from 0-40 wt % water, or 0-30 wt % water, or 0-20 wt % water, or 0-10 wt % water, or wherein the hydrogel is anhydrous.

2.13. Hydrogel 2 or any of 2.1-2.12, wherein the hydrogel is a paste, tablet, powder, spray, serum, patch, non-woven microfiber sheet, foaming mousse, or wafer.

2.14. Hydrogel 2 or any of 2.1-2.13, wherein the hydrogel comprises the carrier in an amount of 20 to 90 wt %, e.g., 30 to 90 wt %, or 40 to 90 wt %, or 50 to 90 wt %, or 60 to 90 wt %, or 70 to 80 wt %, or 70 to 90 wt %.

2.15. Hydrogel 2 or any of 2.1-2.14, wherein the hydrogel further comprises one or more of (c) a linear PEG/PPG triblock copolymer and a polypropylene glycol (PPG)-SMDI copolymer, (d) an polyethylene glycol (PEG) polymer, (e) a polyacrylic acid or polyacrylate polymer (e.g., acrylic acid homopolymer), (f) high-molecular weight hyaluronic acid or an alkali metal hyaluronate polymer (>100,000 Da), and (g) one or more active agents (e.g., antibacterial agents or antifungal agents).

2.16. Hydrogel 2.15, wherein the hydrogel further comprises a (c) linear PEG/PPG triblock copolymer and polypropylene glycol (PPG)-SMDI copolymer.

2.17. Hydrogel 2.16, wherein the (c) linear PEG/PPG triblock copolymer and PPG-SMDI copolymer consists of linear PEG/PPG triblock copolymer portions, PPG portions and SMDI portions (e.g., poloxamer 338 or 407 portions, PPG-12 portions, and SMDI portions).

2.18. Hydrogel 2.17, wherein component (c) is a mixture of the linear PEG/PPG triblock copolymer and a copolymer of PPG and SMDI.

2.19. Hydrogel 2.17, wherein the component (c) is a linear PEG/PPG triblock copolymer covalently linked to a copolymer of PPG and SMDI (e.g., poloxamer 338 or 407 covalently linked to a PPG-12/SMDI copolymer).

2.20. Hydrogel 2.17, wherein the component (c) is a linear PEG/PPG triblock copolymer cross-linked with a copolymer of PPG and SMDI (e.g., poloxamer 338 or 407 cross-linked with a PPG-12/SMDI copolymer).

2.21. Hydrogel 2.17, wherein the PPG (e.g., PPG-12) is condensed with SMDI.

2.22. Hydrogel 2.17, wherein the linear PEG/PPG triblock copolymer is condensed with SMDI (e.g., poloxamer 338 or 407 condensed with SMDI).

2.23. Hydrogel 2.17, wherein the linear PEG/PPG triblock copolymer and the PPG are both condensed with SMDI (e.g., with condensation occurring between the SMDI and the hydroxy termini of the PEG/PPG triblock copolymer, e.g., poloxamer 338 or poloxamer 407, and/or the PPG, e.g., PPG-12).

2.24. Any of Hydrogels 2.17-2.23, wherein the PPG has an average n value (average number of moles of propylene oxide in the polymer) of 3 to 70.

2.25. Hydrogel 2.24, wherein the PPG has an average n value of 3 to 30, or 3 to 20, or 7 to 16, or 9 to 15, or about 12 (e.g., the PPG is PPG-12).

2.26. Any of Hydrogels 2.17-2.25, wherein the (c) component linear PEG/PPG triblock copolymer has the structure HO—$[CH_2CH_2O]_a$[—$CH(CH_3)CH_2O$—$]_b$ $[CH_2CH_2O]_a$—H, wherein a is an integer between 100 and 200, b is an integer between 30 and 80.

2.27. Hydrogel 2.26, wherein the (c) component linear PEG/PPG triblock copolymer has said structure wherein a is an integer between 125 and 175 and b is an integer between 30 and 70, or wherein a is an integer between 135 and 165, and b is an integer between 40 and 60, or wherein a is an integer between 140 and 150 and b is an integer between 40 and 50, or wherein a is about 141, and b is about 44.

2.28. Hydrogel 2.26 or 2.27 wherein the (c) component linear PEG/PPG triblock copolymer has a PPG core molecular weight of about 2000 to 5000 Da, or about 2500 to 4000 Da, or about 3000 to 3500 Da, or about 3300 Da.

2.29. Any of Hydrogels 2.26-2.28, wherein the (c) component linear PEG/PPG triblock copolymer has a polyethylene oxide content of about 70 to 90% by weight, e.g., about 80% by weight.

2.30. Any of Hydrogels 2.26-2.29, wherein the (c) component linear PEG/PPG triblock copolymer is poloxamer 338.

2.31. Any of Hydrogels 2.17-2.25, wherein the (c) component linear PEG/PPG triblock copolymer has the structure HO—$[CH_2CH_2O]_a$[—$CH(CH_3)CH_2O$—$]_b$ $[CH_2CH_2O]_a$—H, wherein a is an integer between 50 and 130, b is an integer between 30 and 80.

2.32. Hydrogel 2.31, wherein the (c) component linear PEG/PPG triblock copolymer has said structure wherein a is an integer between 75 and 125 and b is an integer between 50 and 70, or wherein a is an integer between 85 and 115, and b is an integer between 55 and 65, or wherein a is an integer between 90 and 110 and b is an integer between 55 and 60, or wherein a is an integer between 95 and 105 and b is an integer between 55 and 60, or wherein a is an integer between 98 and 101, and b is about 56.

2.33. Hydrogel 2.31 or 2.32 wherein the (c) component linear PEG/PPG triblock copolymer has a PPG core molecular weight of about 2500 to 5000 Da, or about 3000 to 4500 Da, or about 3500 to 4100 Da, or about 3500 to 3700 Da, or about 3700 to 4100 Da, or about 3600 Da or about 4000 Da.

2.34. Any of Hydrogels 2.31-2.33, wherein the (c) component linear PEG/PPG triblock copolymer has a polyethylene oxide content of about 60 to 80% by weight, e.g., about 70% by weight.

2.35. Any of Hydrogels 2.31-2.34, wherein the (c) component linear PEG/PPG triblock copolymer has a molecular weight of 5000 to 25,000 Da, or about 7000 to 20,000 Da, or about 8000 to 16,000 Da, or about 9000 to 15,000 Da, or about 9840 to 14,600 Da.

2.36. Any of Hydrogels 2.31-2.35, wherein the (c) component PEG/PPG triblock copolymer has an HLB (hydrophilic-lipophilic balance) value of 18-22

2.37. Any of Hydrogels 2.31-2.36, wherein the (c) component linear PEG/PPG triblock copolymer is Poloxamer 407.

2.38. Any of Hydrogels 2.16-2.37, wherein component (c) is ExpertGel 412 (e.g., a poloxamer 407/PPG-12/SMDI copolymer).

2.39. Any of Hydrogels 2.16-2.38, wherein component (c) is ExpertGel 312 (e.g., a poloxamer 338/PPG-12/SMDI copolymer).

2.40. Any of Hydrogels 2.16-2.39, wherein the hydrogel comprises component (c) (e.g., ExpertGel 312 or ExpertGel 412) in an amount of 1 to 20 wt %, e.g., 5-15 wt % or 5-10 wt % or 8 to 12 wt % or about 10 wt %.

2.41. Any of Hydrogels 2.15-2.40, wherein the hydrogel further comprises a polyethylene glycol (PEG) polymer.

2.42. Hydrogel 2.41, wherein the PEG polymer has an average molecular weight of 400 to 20,000 (i.e., PEG-400 to PEG-20,000).

2.43. Hydrogel 2.42, wherein the PEG polymer has an average molecular weight of 2000 to 12,000 (i.e., PEG-2000 to PEG-12000).

2.44. Hydrogel 2.42, or 2.43, wherein the PEG polymer has an average molecular weight of 6000 to 10,000 Da (i.e., PEG-6000 to PEG-10000).

2.45. Any of Hydrogels 2.42-2.44, wherein the hydrogel comprises PEG-6000, PEG-8000, PEG-10000, or a combination thereof.

2.46. Any of Hydrogels 2.42-2.45, wherein the hydrogel comprises PEG polymer in an amount of 0.1 to 3 wt %, e.g., 0.1 to 2 wt %, or 0.1 to 1 wt %, or 0.1-0.5 wt %, or 0.5-1 wt %.

2.47. Hydrogel 2 or any of 2.15-2.46, wherein the hydrogel further comprises a polyacrylic acid or polyacrylate polymer (e.g., acrylic acid homopolymer), such a Carbomer homopolymer Type A.

2.48. Hydrogel 2.47, wherein the polyacrylic acid or polyacrylate polymer is a cross-linked polymer, e.g., cross-linked with allyl sucrose or allyl pentaerythritol.

2.49. Hydrogel 2.48, wherein the polyacrylic acid or polyacrylate polymer is a highly cross-linked polymer, e.g., having a viscosity of 29,000 to 40,000 mPa-s, such as Carbomer 974P NF.

2.50. Hydrogel 2.48, wherein the polyacrylic acid or polyacrylate polymer is a lightly cross-linked polymer, e.g., having a viscosity of 4,000 to 11,000 mPa-s, such as Carbomer 971P NF.

2.51. Any of Hydrogels 2.47-2.50, wherein the hydrogel comprises the polyacrylic acid or polyacrylate polymer in an amount of 0.05 to 5 wt %, e.g., 0.1 to 2 wt %, or 0.1 to 1 wt %, or 0.1 to 0.5 wt %, or about 0.3 wt %.

2.52. Any of Hydrogels 2.15 to 2.51, wherein the hydrogel further comprises a high-molecular weight hyaluronic acid or an alkali metal hyaluronate polymer (>100,000 Da).

2.53. Hydrogel 2.52, wherein the hyaluronic acid or alkali metal hyaluronate polymer has an average molecular weight of 200,000 to 1,500,000 Da, e.g., 300,000 to 1,200,000 Da, or 300,000 to 700,000 Da, or 700,000 to 1,100,000 Da, or 300,000 to 450,000, or 350,000 to 600,000 Da, or 900,000 to 1,100,000 Da, or 250,000 to 700,000 Da, or 250,000 to 500,000 Da, or 250,000 to 350,000 Da, or about 290,000 Da, or about 315,000 Da, or about 370,000 Da, or about 480,000 Da, or about 1,000,000 Da.

2.54. Hydrogel 2.52 or 2.53, wherein the hyaluronic acid or alkali metal hyaluronate polymer is sodium hyaluronate polymer.

2.55. Any of Hydrogels 2.52-2.54, wherein the hydrogel comprises the hyaluronic acid or alkali metal hyaluronate polymer in an amount of 0.05 to 5 wt %, e.g., 0.1 to 2 wt %, or 0.1 to 1 wt %, or 0.3 to 0.5 wt %, or about 0.4 wt %; and optionally, wherein the weight ratio of the linear PEG/PPG triblock copolymer (e.g., Pluronic F-127) to the hyaluronic acid or alkali metal hyaluronate polymer is 10:1 to 30:1, e.g., 10:1 to 25:1, or 10:1 to 20:1, or 10:1 to 15:1 or about 12.5:1.

2.56. Hydrogel 2, or any of 2.1-2.55, wherein the hydrogel further comprises one or more active agents (e.g., antibacterial agents or antifungal agents).

2.57. Hydrogel 2.56, wherein the active agent is selected from zinc salts, stannous salts, quaternary ammonium compounds, guanidines, amino acids, amino acid complexes, fluoride ion sources, tetrahydrocurcumin, vitamins, antibacterial agents, antifungal agents, anti-sensitivity agents, anti-inflammatory agents, anesthetic agents (e.g., local anesthetics), essential oils, and combinations thereof.

2.58. Hydrogel 2.57, wherein the active agent is selected from zinc oxide, zinc citrate, zinc sulfate, zinc chloride, zinc phosphate, zinc lactate, zinc pyrophosphate, zinc salicylate, zinc picolinate, stannous chloride, stannous fluoride, stannous pyrophosphate, cetylpyridinium chloride, benzalkonium chloride, chlorhexidine (e.g., chlorhexidine gluconate), arginine (e.g., arginine carbonate, arginine bicarbonate, arginine hydrochloride), lysine, histidine, zinc-bislysine-chloride complexes, zinc-bisarginine-chloride complexes, sodium fluoride, sodium monofluorophosphate, amine fluorides, tetrahydrocurcumin, eugenol, nicotinamide, riboflavin, sodium nitrate, potassium nitrate, strontium nitrate, eucalyptol, thymol, menthol, hydrogen peroxide, doxycycline, minocycline, ketoconazole, or combinations thereof.

2.59. Hydrogel 2.58, wherein the active agent is zinc oxide, cetylpyridinium chloride, chlorhexidine gluconate, eugenol, or a combination thereof.

2.60. Any of Hydrogels 2.56 to 2.59, wherein each active agent is present in an amount of 0.01 to 5 wt %, e.g., 0.05 to 2.5%, or 0.1 to 1%, or 0.05 to 0.5 wt %.

2.61. Hydrogel 2.59, wherein the hydrogel comprises zinc oxide in an amount of 0.1 to 1 wt %, e.g., about 0.5 wt %; and/or cetylpyridinium chloride in an amount of 0.01 to 0.2%, e.g., about 0.015% or about 0.075 wt % and/or chlorhexidine gluconate in an amount of 0.1 to 5%, e.g., about 2.5% or about 5%; and/or eugenol in an amount of 0.1 to 0.5%, e.g., about 0.3%.

2.62. Hydrogel 2, or any of 2.1-2.61, wherein the hydrogel further comprises one or more thickeners (e.g., cellulose derivatives, silicas, arginine, or carbonate salts).

2.63. Hydrogel 2.62, wherein the one or more thickeners are selected from carboxymethyl cellulose (e.g., sodium CMC), silica, calcium carbonate, sodium carbonate, and arginine carbonate).

2.64. Hydrogel 2.62 or 2.63, wherein the hydrogel comprises each of the one or more thickeners in an amount of 0.5 to 50 wt %, e.g., 0.5 to 10 wt %, or 0.5 to 5 wt %, or 0.5 to 3 wt %, or 5-50 wt %, or 5 to 30 wt %, or 5 to 20 wt %, or 5 to 15 wt %, or 15 to 40 wt %, or 15 to 30 wt %.

2.65. Hydrogel 2.63 or 2.64, wherein the hydrogel comprises carboxymethyl cellulose in an amount of 0.5 to 10 wt %, e.g., 0.5 to 5 wt %, or 0.5 to 3 wt %, or about 0.5, 1.0, or 1.5 wt %.

2.66. Any of hydrogels 2.63-2.65, wherein the hydrogel comprises one or more silicas in a net amount of 5 to 50 wt %, e.g., 8 to 35 wt %, or 10 to 30 wt %, or 10 to 20 wt %.

2.67. Any of hydrogels 2.63-2.66, wherein the hydrogel comprises calcium carbonate in an amount of 5 to 50 wt %, e.g., 10 to 40 wt %, or 25 to 35 wt %, or 10 to 20 wt %.

2.68. Any of hydrogels 2.62-2.67, wherein the hydrogel comprises arginine.

2.69. Hydrogel 2.68, wherein the hydrogel comprises arginine in an amount of 1 to 30 wt %, e.g., 1 to 20 wt %, or 10 to 20 wt %, or 1 to 10 wt %.

2.70. Hydrogel 2, or any of 2.1-2.69, further comprising one or more preservatives (e.g., benzyl alcohol), coloring agents, flavoring agents (e.g., eugenol), sweeteners, buffers (e.g., acids or bases), or other oral care ingredients, for example, each in an amount of less than 0.5 wt %, or less than 0.3 wt %, or less than 0.1 wt %, or less than 0.05 wt %.

2.71. Hydrogel 2, or any of 2.1-2.70, wherein the hydrogel has a pH of 5.5 to 6.5 (e.g., 5.5 to 6.0).

2.72. Hydrogel 2, or any of 2.1-2.71, wherein the hydrogel is an amorphous solid or semisolid but absorbs water to form a viscous gel in the oral cavity (e.g., in the periodontal cavity).

2.73. Hydrogel 2.72, wherein the hydrogel is a dry, non-hygroscopic solid or semi-solid at a temperature below 30° C. (e.g., at 20-30° C. or at about 25° C.) which does not absorb significant amounts of water from the air.

2.74. Hydrogel 2.73, wherein the hydrogel rapidly hydrates and forms a viscous gel at a temperature above 30° C. and below 40° C., e.g., at a temperature of 35° C. to 39° C., or 36° C. to 38° C. (e.g., at about 37° C.) and/or at a pH of 6.5 or above (e.g., 7.0 or above).

2.75. Hydrogel 2.74, wherein the viscosity of the resulting viscous gel is at least 100,000 mPa-s, e.g., 100,000 to 5,000,000 mPa-s, or 200,000 to 2,000,000 mPa-s, or 600,000 to 1,400,000 mPa-s, or 800,000 to 1,200,000 mPa-s, or about 1,000,000 mPa-s.

2.76. Hydrogel 2.72-2.75, wherein the resulting viscous gel adheres to the mucous lining of the oral cavity (e.g., the periodontal cavity or the oral mucosa).

2.77. Hydrogel 2.72-2.76, wherein the resulting viscous gel interacts with mucin to strengthen adherence to the mucosal surface of the oral cavity (e.g., periodontal cavity or the oral mucosa), such as due to rheological synergy with mucin.

2.78. Any of Hydrogels 2.72-2.77, wherein the resulting viscous gel slowly releases any active agent and/or any hyaluronic acid or alkali metal hyaluronate in a sustained manner (e.g., at a rate of 1-20% of the active agent content per day for a period of at least 1 day, such as over 1 to 30 days).

In further embodiments, the present disclosure provides any of Hydrogel 1, or any of 1.1-1.84, or Hydrogel 1A, or Hydrogel 2 or any of 2.1-2.78, wherein the hydrogel is a topical barrier gel or an injectable periodontal gel.

In a third aspect, the present disclosure provides a method of treating or preventing a disease of the oral cavity comprising administering to the oral cavity Hydrogel 1, or any of 1.1-1.84, or Hydrogel 1A, or Hydrogel 2 or any of 2.1-2.78. The present disclosure further provides use of Hydrogel 1, or any of 1.1-1.84, or Hydrogel 1A, or Hydrogel 2 or any of 2.1-2.78, for the treatment or prevention of a disease of the oral cavity. The present disclosure further provides Hydrogel 1 or any of 1.1-1.84, or Hydrogel 1A, or Hydrogel 2 or any of 2.1-2.78, for use in the treatment of prevention of a disease of the oral cavity. In some embodiments of the foregoing aspect, the disease of the oral cavity is periodontal disease (including gingivitis and periodontitis), dental caries, dental hypersensitivity, halitosis, and oral infections (e.g., fungal or bacterial infections of the oral mucosa). In some embodiments, the Hydrogel is administered by injection into the oral cavity, e.g., into the periodontal cavity, the periodontal pocket, or the gingival pocket, such as by using a syringe (e.g., with a narrow bore needle).

In some embodiments, the hydrogel is configured for delivery as an oral spray. In some embodiments, the aforementioned kit comprises such a hydrogel packaged into a container with a finger-tip actuated spray device, optionally with a long-tip for accurate delivery of the spray into small spaces within the oral cavity. In some embodiments, the hydrogel is formulated for injection, e.g., into the periodontal pocket. In some embodiments, the hydrogen is packaged in a container or kit with a syringe and a needle (e.g., metal or plastic) suitable for injection of the hydrogel into the periodontal pocket. In some embodiments, the hydrogel is packaged in a tube (e.g., a squeezable tube) or in a single-use application for application to the tooth (e.g., to a damaged tooth) or the gums or to the oral mucosa or to the dental socket (e.g., following tooth extraction), such as, using an applicator (e.g., a plastic applicator or a cotton-tipped swab) or the tip of a finger (e.g., the patient's finger or a dentist's or dental hygienist's finger).

In further embodiments of the aforementioned methods and uses, Hydrogel 1 or any of 1.1-1.84, or Hydrogel 1A, or Hydrogel 2 or any of 2.1-2.78, is used in a method for, or is effective to:

(i) form a barrier within the oral cavity, e.g., on a damaged surface of a tooth or damaged portion of the gum or oral mucosa, or in or over the dental pocket (e.g., after tooth extraction)
(ii) carry, solubilize, suspend, and/or deliver a drug (e.g., an active agent) to the oral cavity, e.g., to a damaged surface of a tooth or damaged portion of the gum or oral mucosa, or in or over the dental pocket (e.g., after tooth extraction),
(iii) adhere to a surface of the oral cavity, e.g., on a damaged surface of a tooth or damaged portion of the gum or oral mucosa, or in or over the dental pocket (e.g., after tooth extraction), in order to provide a barrier to infection or to deliver a drug (e.g., an active agent) to the oral tissues
(iv) reduce or inhibit formation of dental caries,
(v) reduce, repair or inhibit pre-carious lesions of the enamel, e.g., as detected by quantitative light-induced fluorescence (QLF) or electrical caries measurement (ECM),
(vi) reduce or inhibit demineralization and promote remineralization of the teeth,
(vii) reduce hypersensitivity of the teeth,
(viii) reduce or inhibit gingivitis,
(ix) promote healing of sores or cuts in the mouth,
(x) reduce levels of acid producing and/or malodor producing bacteria,
(xi) increase relative levels of arginolytic bacteria in the mouth,
(xii) inhibit microbial biofilm formation in the oral cavity,
(xiii) raise and/or maintain plaque pH at levels of at least pH 5.5 following sugar challenge,
(xiv) reduce plaque accumulation, and/or
(xv) treat, relieve or reduce dry mouth.

In a further aspect, the present disclosure provides a kit comprising Hydrogel 1 or any of 1.1-1.84, or Hydrogel 1A, or Hydrogel 2 or any of 2.1-2.78, with an oral administration device, such as a syringe and/or needle. Preferably the syringe is a disposable plastic syringe (e.g., polyethylene and/or polypropylene), optionally packaged with a long-tip needle of 21 gauge (21 G) size or narrower (e.g., 21 G to 34 G, 23 G to 32 G, 25 G to 28 G). In some embodiments, the kit comprises an amount of the hydrogel of 0.5 to 1.5 mL (e.g., 0.7 to 1.2 mL). In some embodiments, the kit comprises the hydrogel pre-filled into the syringe. Preferably the needle is a blunt-tip needle (i.e., not a hypodermic needle). Alternatively, the administration device may be an applicator.

The inventors have found that hydrogel compositions as described herein (e.g., Hydrogel 1, or any of 1.1 et seq.) have a low viscosity at ambient temperature, but upon warming to the normal temperature of the oral cavity and/or on exposure to oral pH levels, these liquids undergo a sol-gel phase transition resulting in formation of a viscous gel. Specifically, the hydrogels may be formulated to be free-flowing liquids at ambient temperature having a pH of greater than 7.0 (e.g., 8.0-9.0 or 8.5-9.0). However, upon exposure to either a temperature of about 37° C. (e.g., 35-40° C.) or on exposure to mucin, or any combination of the preceding, the hydrogel undergoes a rapid sol-gel transition to form a high viscosity gel. Without being bound by theory, it is believed that the temperature-dependent aspect of the transition results primarily from the behavior of the poloxamer polymers in the composition, while the pH-dependent aspect of the transition results primarily from the polyacrylate polymers in the composition. This transition is promoted by the acid-base neutralization of the polyacrylate polymers, which leads to swelling of the cross-linked gel network.

The hydrogels according to the present disclosure are also found to unexpectedly interact with the mucin polymers present in the secretions covering normal human oral mucosa. Without being bound by theory, it is believed that the polyacid chains provided by the polyacrylate polymers and/or hyaluronic acid polymer in the compositions results in entanglement with the mucin, which results in modulation of the mucin nanostructure and mesh size. It is believed that the carboxyl and hydroxyl groups of the polymers form intermolecular hydrogen bonds and/or ionic bonds with the glycosyl groups on the mucin polymers, an effect further facilitated by the flexible conformation of high-molecular weight hyaluronic acid. The resulting reduced mesh size may promote exclusion of pathogenic organisms from the mucosal surface.

This gel can then serve as a vehicle for controlled release of a therapeutic agent, e.g., an antibacterial agent, antifungal agents, anticaries agent, anti-hypersensitivity agent, directly into the tissues of the oral cavity over an extended period time without the interference caused by dilution by saliva. In some embodiments, such a composition may be administered into a periodontal pocket, completely or partially filling said pocket, whereupon the liquid will transition to a viscous gel that adheres and remains inside the inflamed pocket, releasing the therapeutic agent in a sustained release manner to thereby treat the underlying periodontal disease.

The terms "periodontal pocket," "periodontal crevice," "gingival pocket," "gingival crevice," and "dental pocket," used herein interchangeably, refer to an abnormal space between the cervical enamel of a tooth and the overlying unattached gingiva, resulting from a chronic inflammatory response associated with untreated gingivitis or periodontitis, which leads to destruction and fracture of the bone and tissue supporting said tooth.

The terms "sustained-release," "extended release," and "controlled release," used herein interchangeably, refer to the release of an active agent from a composition comprising it at predetermined intervals or gradually, in such a manner as to make the contained active agent available over an extended period of time, e.g., hours (e.g., up to 6, 12, 18, 24, 36, or 48 hours), days (e.g., 1-30 days), or weeks (e.g., 1-4 weeks). The release profile of the active agent from the composition of the present disclosure, after turning into a gel, depends on various parameters such as the particular polymers used, and their amounts in the composition; and the ratio (by weight) between the various polymers.

The term "poloxamer" or "poloxamer copolymer" refers to a polyethoxy/polypropoxy block copolymer, i.e., a non-ionic triblock copolymer composed of a central hydrophobic chain of polyoxypropylene units (a.k.a. poly(propylene oxide) units) flanked by two hydrophilic chains of polyoxyethylene units (e.g., poly(ethylene oxide) units). Poloxamers have the following chemical structure:

$$HO—[CH_2CH_2O]_a[—CH(CH_3)CH_2O—]_b[CH_2CH_2O]_a—H,$$

wherein a and b are integers, each typically between 10 and 200. Poloxamers are named according to common conventions based on their molecular weight and ethoxy content, and include poloxamer 407, poloxamer 338, poloxamer 237, poloxamer 188 and poloxamer 124. Pluronic is the name of a line of poloxamer polymers manufactured by BASF. For example, Pluronic F-127 is poloxamer 407. Poloxamers are distinguished from other polyethylene glycol/polypropylene glycol copolymers (PEG/PPG copolymers or EO/PO copolymers) which have a structure other than as a triblock structure, such as a random copolymer structure. Such copolymers that are distinct from poloxamers include the PEG/PPG copolymers sold by BASF as the Pluracare and Pluraflow series polymers.

Carbomers are a generic term for polyacrylic acid polymers, such as the Carbopol brand of polymers sold by Lubrizol.

ExpertGel 312 and ExpertGel 412 are proprietary complex polymers sold by PolymerExpert. ExpertGel 312 is a poloxamer 338 and PPG-12/SMDI copolymer. ExpertGel 412 is a poloxamer 407 and PPG-12/SMDI copolymer. SMDI is saturated methylene diphenyl diisocyanate or saturated methylene dicyclohexyl diisocyanate, also known as 1,1-methylenebis[4-isocyanatobenzene] or 1,1'-methylenebis[4-isocyanatocyclohexane]. SMDI has two isocyanate functional group which may be condensed with the free hydroxyl group of PEG polymers, PPG polymers, or PEG/PPG copolymers (including poloxamers) to form urea (carbamate) linking groups. ExpertGel polymers are further described in, e.g., U.S. Pat. No. 7,339,013, the contents of which are hereby incorporated by reference in its entirety.

Hyaluronic acid is an anionic, non-sulfated glycosaminoglycan (GAG) widely distributed throughout connective tissues of vertebrates, being the most abundant glycosaminoglycan of higher molecular weight in the extracellular matrix of soft periodontal tissues. Hyaluronic acid can exist in its free acid form, or in the form of a salt (such as an alkali metal salt). Hyaluronic acid has important hygroscopic, rheological and viscoelastic properties that fluctuate with changes in temperature, pH, ionic environment, and binding partners. However, these properties are also highly dependent on chain length. Hyaluronic acid can reach over $10^7$ Da in molecular mass, but also exists in multiple smaller forms, referred to as low molecular weight hyaluronan or oligomeric hyaluronan.

Hyaluronan has been found to be effective in the treatment of inflammatory processes in medical fields such as orthopedics, dermatology and ophthalmology, and it has been further found to be anti-inflammatory and antibacterial in gingivitis and periodontitis therapy. Due to its tissue healing properties, it has been suggested for use as an adjunct to mechanical therapy in the treatment of periodontitis. Hyaluronan affects endothelial cell proliferation and monolayer integrity, and also has effects on angiogenesis.

The term "active agent" as used herein refers to any agent having a therapeutic effect that might be beneficial in treatment or prevention of disease in the oral cavity, such as periodontal disease, e.g., an antimicrobial agent, an antibacterial agent, an antifungal agent, an anti-inflammatory agent (e.g., a nonsteroidal anti-inflammatory drug), an anti-sensitivity agent, an anesthetic agent, a tartar-control agent, and a fluoride agent.

Examples of antifungal agents include, without being limited to, fluconazole, itraconazole, amphotericin B, voriconazole, nystatin, clotrimazole, econazole nitrate, miconazole, terbinafine, ketoconazole, enilconazole, boric acid, and miconazole.

The term "non-steroidal anti-inflammatory drug" (NSAID) as used herein refers to any non-steroidal anti-inflammatory drug/agent/analgesic/medicine, and relates to both cyclooxygenase (COX)-2 selective inhibitors such as celecoxib, rofecoxib, valdecoxib, parecoxib, etoricoxib and lumiracoxib, as well as to COX-2 non-selective inhibitors such as etodolac, aspirin, naproxen, ibuprofen, indomethacin, piroxicam and nabumetone.

Examples of anesthetic agents include, without being limited to, a local anesthetic, such as lidocaine, benzocaine, dibucaine, tetracaine, and proparacaine. In addition, eugenol has local anesthetic properties.

Examples of antibacterial agents include zinc salts, e.g., zinc oxide, zinc citrate, zinc lactate, zinc phosphate, zinc pyrophosphate, zinc chloride, zinc nitrate, zinc acetate, zinc gluconate, zinc sulfate; stannous salts, e.g., stannous chloride, stannous fluoride, stannous pyrophosphate, stannous nitrate, stannous sulfate; quaternary ammonium compounds or a pharmaceutically acceptable salt thereof, e.g., benzalkonium chloride, or cetylpyridinium chloride; guanidine compounds or a pharmaceutically acceptable salt thereof, e.g., chlorhexidine (e.g., chlorhexidine gluconate), alexidine, or polyhexamethylene biguanide (PHMB); hexetidine; eucalyptol; menthol; methyl salicylate; thymol; peppermint oil; bispyridinamine octenidine (1,1,4,4'-tetrahydro-N,N'-dioctyl-1,1'-decamethylenedi-(4-pyridylideneamine), or a pharmaceutically acceptable salt thereof, such as octenidine dihydrochloride.

Examples of tartar-control agents include phosphate and polyphosphate salts (for example pyrophosphates and tripolyphosphates), polyaminopropanesulfonic acid (AMPS), hexametaphosphate salts, polyolefin sulfonates, polyolefin phosphates, and diphosphonates. In particular embodiments, these salts are alkali phosphate salts, e.g., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; and dimeric phosphates such as pyrophosphates; and multimeric phosphates, such as tripolyphosphates, tetraphosphates, hexaphosphates and hexametaphosphates (e.g., sodium hexametaphosphate). In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these.

Examples of fluoride agents include stannous fluoride, sodium fluoride, potassium fluoride, sodium monofluorophosphate, sodium fluorosilicate, ammonium fluorosilicate, amine fluoride, ammonium fluoride, and combinations thereof.

In some embodiments, the hydrogel compositions may comprise small amounts of additional polymers (e.g., 0.1-10 wt %, or 0.1-5 wt %, or 0.1 to 3 wt %, or 0.1 to 1 wt %, each of in the aggregate) to further adjust the viscosity of the formulations or to enhance the solubility or stability of an active agent or other component. Such additional polymers include polyethylene glycols, polypropylene glycols, polysaccharides (e.g., cellulose derivatives, for example carboxymethyl cellulose, hydroxypropyl cellulose, hydroxypropyl methyl cellulose, ethyl cellulose, microcrystalline cellulose; or polysaccharide gums, for example xanthan gum, guar gum, or carrageenan gum, karaya gum); polyvinyl pyrrolidone (PVP), such as cross-linked PVP; synthetic anionic polymeric polycarboxylates, such as copolymers of maleic anhydride or acid with another polymerizable ethylenically unsaturated monomer, preferably methyl vinyl ether (e.g., copolymers in a 1:4 to 4:1 ratio of maleic anhydride/acid to methyl vinyl ether). Acidic polymers, for example polyacrylate gels, may be provided in the form of their free acids or partially or fully neutralized water-soluble alkali metal (e.g., potassium and sodium) or ammonium salts. In one embodiment, the oral care composition may contain PVP. PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group.

The term “subject” as used herein refers to any mammal, e.g., a human, non-human primate, horse, ferret, dog, cat, cow, and goat. In a preferred embodiment, the term “subject” denotes a human, i.e., an individual.

The liquid hydrogel solution disclosed herein (i.e., Hydrogel 1 or any of 1.1-1.84) may be packed in a suitable sealed syringe equipped with a suitable blunt needle, wherein the amount of said liquid composition in the syringe may be sufficient for treating varying number of gingival pockets (e.g., about 0.7 ml to about 1.2 ml). Such a syringe may be equipped with a 25 G needle or tip for optimal injection; however, smaller or larger gauges can be used as well. The syringe is best operated at either ambient or below ambient temperature where the viscosity is low enough to allow precise and controlled delivery without exerting excessive pressure. At this temperature, a dentist can deliver the right amount of liquid composition directly into the oral cavity, such as to the bottom of the gingival pocket, where it will turn into gel that will adhere and stay in place. Upon gelation, the highly viscous structure controls the release of the hyaluronic acid or salt and/or any additional active agent present, in a sustained manner, i.e., during hours and up to several days.

In some embodiments, the hydrogels of the present disclosure may be characterized by one or more rheological parameters. Basic parameters include shear stress (tau, $\tau$), shear rate (gamma dot, $\dot{\gamma}$), and shear viscosity (eta, $\eta$), which are related by Newton’s Law as: $\tau=(\dot{\gamma})(\eta)$. Viscosity, shear stress and shear rate are not constant for all substances, however, and may vary based on conditions (e.g., temperature, shear rate). Thus, flow behavior varies. For Newtonian compositions, the viscosity is independent of the shear rate, and thus, a plot of shear stress versus shear rate would yield a straight line whose slope is the shear viscosity. Many substances have non-Newtonian flow behavior. Non-Newtonian flow behavior includes shear thinning behavior, characterized by decreasing viscosity with increasing shear rate, and shear-thickening behavior, characterized by increasing viscosity with increasing shear rate. Another category of compositions are those showing mixed viscous and elastic behavior in response to shear, called viscoelastic compositions.

Viscoelastic behavior is commonly described using the parameters G, G', and G". G is the shear modulus, and it is equal to shear stress ($\tau$) divided by shear strain ($\gamma$). The shear modulus can be resolved into two components, the storage modulus G', and the loss modulus G". These two parameters describe, respectively, the elastic portion (solid-state behavior) of the shear modulus and the viscous portion (liquid state behavior) of the shear modulus. Viscoelastic solids have a G' higher than G" (i.e., G'/G" ratio>1) while viscoelastic liquids have a G" higher than G' (i.e., G'/G" ratio<1). Compositions according to the present disclosure, which display thermosensitive or mucosensitive gelling behavior, preferably have a G'/G" ratio of <1 in the liquid state and >1 in the gelled state.

Unless otherwise indicated, all numbers expressing quantities of ingredients and so forth used in the present description and claims are to be understood as being modified in all instances by the term “about.” Accordingly, unless indicated to the contrary, the numerical parameters set forth in this description and attached claims are approximations that may vary by up to plus or minus 10% depending upon the desired properties sought to be obtained by the present invention.

Unless otherwise specified, all percentages and amounts expressed herein and elsewhere in the specification should be understood to refer to percentages by weight of the entire composition. The amounts given are based on the active weight of the material.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The invention will now be illustrated by the following non limiting Examples.

EXAMPLES

Example 1: Exemplary Aqueous Hydrogel Compositions

The following exemplary aqueous hydrogel compositions are prepared according to the present disclosure (all values are in weight 0%):

| Ingredient | Fm. 1-1 | Fm. 1-2 | Fm. 1-3 | Fm. 1-4 | Fm. 1-5 | Fm. 1-6 | Fm.1-7 |
|---|---|---|---|---|---|---|---|
| Water | Q.S. (~84%) | Q.S. (~89%) | Q.S. (~84%) | Q.S. (~84%) | Q.S. (~89%) | Q.S. (~84%) | Q.S. (~84%) |
| Poloxamer 407 (Pluronic F-127 NF) | 5 | 3.33 | 5 | 5 | 3.33 | 5 | 5 |
| Carbomer 971P | 0.3 | | | | | | |
| Carbomer 974P | | 0.2 | 0.3 | 0.3 | 0.2 | 0.3 | 0.3 |
| EG312 (Poloxamer 338 + PPG-12/SMDI Copolymer) | 10 | 6.66 | 10 | 10 | 6.66 | 10 | 10 |
| Hyaluronic Acid Sodium (high-MW) | 0.4 | | | | | | |
| Hyaluronic acid (high-MW) | | 0.2 | 0.2 | 0.2 | 0.2 | 0.2 | 0.2 |
| CPC | 0.075 | 0.075 | 0.075 | 0.075 | 0.075 | 0.075 | 0.075 |
| Zinc Oxide | 0.5 | 0.5 | 0.5 | 0.5 | 0.5 | 0.5 | 0.5 |
| NaOH (50% Aq) | 0.08 | | | | | | |
| Benzyl alcohol | | | | | 0.3 | 0.3 | |
| Riboflavin | | | | | | | 0.01 |
| Color | | | | 0.002 | | | |

| Ingredient | Fm. 1-8 | Fm. 1-9 | Fm. 1-10 | Fm. 1-11 |
|---|---|---|---|---|
| Water | Q.S. (~84%) | Q.S. (~84%) | Q.S. (~84%) | Q.S. (~84%) |
| Poloxamer 407 (Pluronic F-127 NF) | 5 | 5 | 5 | 5 |
| Carbomer 971P | 0.3 | 0.3 | 0.3 | 0.3 |
| EG312 (Poloxamer 338 + PPG-12/SMDI Copolymer) | 10 | 10 | 10 | 10 |
| Hyaluronic Acid (high-MW) | 0.2 (1 MDa) | 0.2 (480 kDa) | 0.4 (480 kDa) | 0.7 (480 kDa) |
| CPC | 0.075 | 0.075 | 0.075 | 0.075 |
| Zinc Oxide | 0.5 | 0.5 | 0.5 | 0.5 |
| NaOH (50% Aq) | 0.00 | 0.15 | 0.15 | 0.15 |

Hydrogels are prepared using a cold process. Formula amounts of carbomer followed by hyaluronic acid are dissolved via homogenization into demineralized water. Zinc oxide is then dispersed into the solution, and the resulting suspension is transferred into an ice bath for cooling. Formula amounts of poloxamer 407 and ExpertGel 312 are added, followed by mixing until dissolution is complete. CPC is then added and the suspension is mixed in an ice bath for at least 60 minutes. The pH is then adjusted to about 9 using 50% aqueous sodium hydroxide.

Example 2: Exemplary Aqueous/Polyol Hydrogel Compositions

The following exemplary aqueous hydrogel compositions comprising polyol humectants are prepared according to the present disclosure (all values are in weight %):

| Formula | Pol. 407 | EG312 | Carbopol 971P | Glyc. | PG | NaOH 25% | HA, 1 MDa | CHX, 20% | CPC |
|---|---|---|---|---|---|---|---|---|---|
| 2-1 | 1.8 | 17.8 | 0 | 10 | 0 | 0.02 | 0 | 0.6 | 0.015 |
| 2-2 | 1.8 | 17.8 | 0.1 | 10 | 0 | 0.14 | 0 | 0.6 | 0.015 |
| 2-3 | 1.8 | 17.8 | 0.2 | 10 | 0 | 0.27 | 0 | 0.6 | 0.015 |
| 2-4 | 1.8 | 17.8 | 0.5 | 10 | 0 | 0.66 | 0 | 0.6 | 0.015 |
| 2-5 | 1.8 | 17.8 | 1.0 | 10 | 0 | 1.20 | 0 | 0.6 | 0.015 |
| 2-6 | 0.45 | 4.5 | 0 | 10 | 0 | 0.02 | 0 | 0.6 | 0.015 |
| 2-7 | 0.45 | 4.5 | 0.1 | 10 | 0 | 0.16 | 0 | 0.6 | 0.015 |
| 2-8 | 0.45 | 4.5 | 0.2 | 10 | 0 | 0.33 | 0 | 0.6 | 0.015 |
| 2-9 | 0.45 | 4.5 | 0.5 | 10 | 0 | 0.68 | 0 | 0.6 | 0.015 |
| 2-10 | 0.45 | 4.5 | 1.0 | 10 | 0 | 1.40 | 0 | 0.6 | 0.015 |
| 2-11 | 1.8 | 17.8 | 0 | 0 | 7 | 0 | 0 | 0.6 | 0.015 |
| 2-12 | 1.8 | 17.8 | 0.1 | 0 | 7 | 0.12 | 0 | 0.6 | 0.015 |
| 2-13 | 1.8 | 17.8 | 0.2 | 0 | 7 | 0.26 | 0 | 0.6 | 0.015 |
| 2-14 | 1.8 | 17.8 | 0 | 0 | 3 | 0 | 0 | 0.6 | 0.015 |
| 2-15 | 1.8 | 17.8 | 0.15 | 0 | 3 | 0.18 | 0 | 0.6 | 0.015 |
| 2-16 | 1.8 | 17.8 | 0.3 | 0 | 3 | 0.36 | 0 | 0.6 | 0.015 |

-continued

| Formula | Plur. F-127 | EG312 | Carbopol 971P | Glyc. | PG | NaOH 25% | HA, 1 MDa | ZnO | CPC |
|---|---|---|---|---|---|---|---|---|---|
| 2-17 | 1.8 | 17.8 | 0 | 0 | 0 | 0 | 0 | 0.6 | 0.015 |
| 2-18 | 1.8 | 17.8 | 0.3 | 0 | 3 | 0.36 | 0 | 0.6 | 0.015 |
| 2-19 | 10 | 0 | 0.4 | 0 | 3 | 0.4 | 0.2 | 0 | 0 |
| 2-20 | 0.45 | 4.5 | 0.3 | 10 | 0 | 0.4 | 0.2 | 0 | 0.015 |
| 2-21 | 4.9 | 0 | 0.3 | 10 | 0 | 0.4 | 0.2 | 0 | 0.015 |
| 2-22 | 0.45 | 4.5 | 0.3 | 10 | 0 | 0.4 | 0 | 0 | 0.015 |
| 2-23 | 20 | 0 | 0.3 | 10 | 0 | 0.4 | 0.2 | 0 | 0.015 |
| 2-24 | 20 | 0 | 0.4 | 0 | 3 | 0.4 | 0.2 | 0 | 0 |
| 2-25 | 5 | 10 | 0.3 | 0 | 0 | 0 | 0.2 | 0.5 | 0.075 |
| 2-26 | 3.3 | 6.7 | 0.2 | 0 | 0 | 0 | 0.2 | 0.5 | 0.075 |

All of the formulas above contained water to Q.S (67-86%), and minor amounts of sweetener, flavor and/or color (<0.25% net).

Rheological behavior (viscosity measurements) as a function of temperature are completed on selected hydrogel formulas.

| Formula | Brookfield Viscosity, 25° C. (cP) | Brookfield Viscosity, 37° C. (cP) | Ratio |
|---|---|---|---|
| 2-6 | 48 | 2730 | 57 |
| 2-7 | 131 | 7880 | 60 |
| 2-8 | 183 | 5640 | 31 |
| 2-9 | 4960 | 12800 | 3 |
| 2-10 | 4600 | 6400 | 1 |
| 2-1 | 785 | 331,000 | 422 |
| 2-2 | 452 | 289,000 | 639 |
| 2-3 | 1,220 | 470,000 | 385 |
| 2-4 | 6,450 | 1,080,000 | 167 |
| 2-5 | 13,960 | 1,560,000 | 112 |

Brookfield Viscosity is measured on a Brookfield HA-DV2 viscometer using a V74 vane spindle. The viscometer applies a user-controlled angular velocity to the spindle, typically measured in rotations per second (RPM), and reports the torque on the shaft of the spindle. Brookfield Viscosity is then calculated from the RPM and torque varies according to the instrument operating instructions using two conversion parameter (shear rate constant, 0.2723; and spindle multiplier constant, 290). The test is performed at both 25° C. and 37° C. The reported Brookfield viscosity readings are taken at 1 RPM.

The results show that carbomer concentration must be fine-tuned in the formulation to avoid losing the desired thermosensitive properties. Preferably, carbomer levels should range from 0.2 to 0.5% in these formulas. Including glycerin and formulating at high levels of gelling agents did not change this trend. An increase in the ratio between hydrogel viscosity at 37° C. and room temperature was observed between 0.2 to 0.5% carbomer in these systems.

The addition of low levels of hyaluronic acid (0.2%, 1M Da) and zinc oxide (0.5%), as shown in Formulas 2-25 and 2-26, did not alter the thermosensitivity of the hydrogel formula.

| Formula | Brookfield Viscosity, 25° C. (cP) | Brookfield Viscosity, 37° C. (cP) | Ratio |
|---|---|---|---|
| 2-25 | 5,580 | 1,020,000 | 183 |
| 2-26 | 173 | 55,200 | 318 |

Example 3: Rheological Synergy with Mucin

Charged mucoadhesive polymers are thought to interact with mucin through a process called "rheological synergism." This means that the viscosity of a solution with mucin is greater than the sum of the viscosities of the polymer and mucin solution separately. This experiment aims to evaluate whether the inventive hydrogel compositions interact synergistically with mucin in this way.

Rheological synergy, a correlative to mucoadhesion can be measured in vitro via rheological profiling of a material in the presence and absence of mucin:

$$\Delta G' = G'_{mix} - (G'_f + G'_m)$$

where $G'_f$, $G'_m$, and G'mix are the elastic moduli for the polymeric formulation, the mucin solution, and the mixture of polymeric formulation and mucin. If the blend of hydrogel and mucin has a greater viscoelastic property than the sum of the gel and mucin alone the polymeric material has mucoadhesive properties.

Generally, a portion of hydrogel is combined with mucin (10%) and a temperature sweep is performed for comparison to the matching control not containing mucin, with rheological profiles quantified. The elastic moduli (G') at 37° C. is compared according to the above equation for samples with and without mucin to determine mucoadhesion at near rheological conditions. An increase in delta G' indicates rheological synergism and mucoadhesive potential.

Three test formulations are prepared according to the table below. All values are in weight percent. EG312 is ExpertGel 312. CPC is cetylpyridinium chloride. CHX is chlorhexidine:

| Formula | Pol. 407 | EG312 | 971P | 1 MDa HA | Glycerin | CPC | NaOH 25% | Water | Flavor/ Color |
|---|---|---|---|---|---|---|---|---|---|
| 3-A | 0.45 | 4.45 | 0 | 0 | 10 | 0.015 | 0.02 | Q.S. (~85) | 0.2 |
| 3-B | 0.45 | 4.45 | 0.3 | 0.2 | 10 | 0.015 | 0.40 | Q.S. (~84) | 0.2 |
| 3-C | 0.45 | 4.46 | 0.15 | 0.2 | 10 | 0.015 | 0.20 | Q.S. (~84) | 0.2 |

Mucin solution is prepared by dispersing mucin in water to a final concentration of 10% w/w. 10 g of hydrogel test sample is combined with 1.11 g of the mucin solution and the mixture is blended to form a slurry. Rheological parameters are determined using an AR1000 rheometer by TA Instruments with a 40 mm diameter parallel-plate geometry with temperature of the lower plate controlled by thermoelectric heating/cooling (Peltier effect).

Here the results of the two experiments are reported, both using a TA Instruments AR1000 rheometer. Both are carried out on samples stored at 4° C. In the first experiment, the sample is placed into a 1 mm gap between the two plates and the temperature is swept up from 4° C. to 37° C. at the heating rate of 0.0435 degrees per second. Viscoelastic moduli, G' and G", are measured once the temperature reaches the target temperature of 37° C. In the second experiment, the sample is placed into a 0.5 mm gap between the two plates and the settings for temperature are abruptly changed from 4° C. to 37° C. The actual temperature, as read by the rheometer, reaches 30° C. in 30 seconds and 37° C. in 60 seconds. After 300 seconds the shear stress ramp test is performed. In this test, shear stress is ramped up at the rate of 10 Pa per second. Viscosity is measured as it reaches the maximum which is reported below as maximum instantaneous viscosity (ViscMax). The stress at which this maximum is reached is reported as Yield Stress (YS). The aforementioned parameters are determined for the mucin dispersion alone, each test composition alone, and for a 10% w/w dilution of each test composition in the mucin dispersion. The following results are obtained (all values are at 37° C.):

| Sample | Yield Stress (Pa) | ViscMax (Pa-s) | G' (Pa) |
|---|---|---|---|
| Mucin dispersion | 0 | <1 | 0.15 |
| Formula 3-A | 35 | 25 | 18 |
| Formula 3-A + mucin | 55 | 163 | 243 |
| Formula 3-B | 35 | 111 | 165 |
| Formula 3-B + mucin | 45 | 170 | 240 |
| Formula 3-C | 35 | 80 | 103 |
| Formula 3-C + mucin | 45 | 170 | 217 |

These results demonstrate a synergistic increase in viscosity and elastic modulus for the mucin/hydrogel combinations tested. The effect of added hyaluronic acid (370 kDa, 0.20 wt %) is also determined for the composition 3-A. The results are shown below (all values are at 37° C.):

| Sample | Yield Stress (Pa) | ViscMax (Pa-s) | G' (Pa) |
|---|---|---|---|
| Mucin dispersion | 0 | <1 | 0.15 |
| Formula 3-A | 35 | 25 | 18 |
| Formula 3-A + mucin | 55 | 163 | 243 |
| Formula 3-A + HA | 25 | 47 | 55 |
| Formula 3-A + mucin + HA | 45 | 139 | 276 |

These results show that the addition of hyaluronic acid increases the viscosity of the samples, but does not inhibit the synergistic increase in viscosity and elastic modulus observed with mucin addition.

Examining the temperature dependence (temperature sweep experiment) of the elastic modulus G' over the range of 5 to 40° C., it is found that for the mucin dispersion alone, G' steadily decreases with increasing temperature. In contrast, each of compositions 3-A, 3-B and 3-C show a steady decrease in G' from 5 to about 25-30° C., followed by a sharp increase in G' from 25-30° C. to 37° C. The sharpness of this transition is most pronounced for formula 3-A. The combination of the compositions with mucin is found to unexpectedly push the G' inflection point to a lower temperature, about 15° C. for each combination, also with a higher G' value at the highest temperature compared to each composition alone. It is further found that the combination of Formula 3-A with hyaluronic acid has only a moderate effect on the G' trace, resulting in a consistently slightly lower G' from 5 to 25° C. with similar higher temperature behavior. In contrast, the combination of Formula 3-A, mucin and hyaluronic acid shows a consistently slightly higher G' over the entire course of the temperature sweep. These results demonstrate that the hydrogels according to the disclosure synergistically interact with mucin to promote gelation at all relevant temperatures, with more formation of a viscous gel at high temperatures (above ambient temperature). The results further show that the synergistic reaction with mucin promotes stronger gelation at lower temperatures compared to the absence of mucin.

The experiment outlined above is repeated using additional gel samples 3-D, 3-E, and 3-F. These four samples have the same composition, shown below, but are different batches prepared at different times:

| Formula | Pol. 407 | EG312 | Carbopol 971P | HA (480 kDa) | CPC | ZnO | NaOH 25% | Water |
|---|---|---|---|---|---|---|---|---|
| 3-D/E/F | 5 | 10 | 0.3 | 0.4 | 0.075 | 0.5 | 0.15 | QS (84) |

The results are shown in the table below (all values are at 37° C.):

| Sample | Yield Stress (Pa) | ViscMax (Pa-s) | G (Pa) | G" (Pa) | G'/G" |
|---|---|---|---|---|---|
| Formula 3-D | 264.5 | 1922 | 3251 | 3210 | 1.013 |
| Formula 3-D + mucin | 194.1 | 9360 | 5816 | 1824 | 3.189 |
| Formula 3-E | 224.8 | 1463 | 2343 | 2772 | 0.845 |
| Formula 3-E + mucin | 224.8 | 10550 | 5768 | 1809 | 3.189 |
| Formula 3-F | 234.4 | 1599 | 2474 | 2752 | 0.899 |
| Formula 3-F + mucin | 214.6 | 10260 | 6261 | 1973 | 3.173 |

Example 4: Sustained Release of Agents

Hydrogel formulations according to the following formulas are prepared as previously described:

| | Formula 4-A | Formula 4-B | Formula 4-C |
|---|---|---|---|
| Poloxamer 407 (%) | 20 | | 5.75 |
| Expert Gel 312 (%) | | 10 | 5.90 |
| Expert Gel 412 (%) | | 10 | 5.25 |
| PEG 8K (%) | | 0.7 | 0.5 |
| Water % | 79 | 78.3 | 81.6 |
| FD&C Blue 1 (%) | 1 | 1 | 1 |

The test formulas are ice chilled and then loaded with the FD&C Blue dye via dispersion with a Speed Mixing apparatus (FlackTek, Inc). Samples are stored at 4° C. overnight. Aliquots (250 μL) of each cold gel are then placed in the wells of a chilled 24 well plate. The well plate is heated at 37° C. for 30 minutes to gel the system. An aliquot (1 mL) of artificial saliva or DI water (both warmed to 37° C.) is added to each well and the plate incubated on an orbital shaker at 90 rpm. Aliquots (3 μL) from each well are removed at the noted timepoints (5, 20, 40, 60, 90, 120, 180, and 360 minutes) and diluted in DI water (270 μL). The amount of FD&C Blue dye removed from the gel is quantified via UV visible spectrophotometer analysis at 288 nm and 630 nm. The results were compared to a standard curve of FD&C Blue 1 (0.005 mg/ml-0.5 mg/ml) in DI water and dilute (1:100) artificial saliva. Controlled release of the dye was observed over the course of 6 hours with different profiles in artificial saliva and di water. The results are summarized in the table below (showing cumulative μg of gel released by mass):

| Solvent | Time (min) | Form. 4-A Av (μg) | Form. 4-B Av (μg) | Form. 4-C Av (μg) |
|---|---|---|---|---|
| Artificial Saliva | 5 | 38.3 | 16.7 | 35.8 |
| | 20 | 187.4 | 285.9 | 190.9 |
| | 40 | 230.5 | 149.4 | 213.8 |
| | 60 | 348.2 | 318.7 | 296.0 |
| | 90 | 484.9 | 401.7 | 479.4 |
| | 120 | 681.9 | 602.0 | 549.5 |
| | 180 | 1006.8 | 864.7 | 823.6 |
| | 360 | 1407.4 | 1540.0 | 1519.4 |
| | 1440 | 1985.2 | 2337.5 | 2318.9 |
| Water | 5 | 59.3 | 66.0 | 66.0 |
| | 20 | 213.3 | 250.4 | 235.1 |
| | 40 | 509.2 | 523.3 | 475.7 |
| | 60 | 811.0 | 1043.5 | 714.8 |
| | 90 | 1108.9 | 988.9 | 1122.9 |
| | 120 | 1417.6 | 1505.9 | 1437.6 |
| | 180 | 1563.7 | 1947.2 | 1871.8 |
| | 360 | 1934.1 | 2686.0 | 2264.1 |
| | 1440 | 2202.9 | 2937.5 | 2736.7 |

These results show that the entrapped agent, FD&C Blue 1 dye, is gradually released from the gel, with a significantly lower rate of release in artificial saliva compared to water. In a similar set of experiments, it is found that zinc salicylate entrained in the gel at concentrations from 2% a to 10% w/w also undergoes a similar, steady release over a six-hour period.

Example 5: Controlled Degradation of Hydrogel in Saliva

The controlled degradation of the hydrogel is demonstrated in vitro under conditions representative of the oral environment. Samples of Hydrogel 2-25 (0.5 mL) are placed into 3 μm transwells cell culture inserts and placed within clarified artificial saliva (1.5 mL) at 37° C. The amount of zinc leached into the salivary medium is quantified over the course of 50 days (1 mL removed for analysis at each timepoint). Gel degradation is correlated to the release of zinc into the salivary medium, as measured via ICP-AES. Results are shown in the table below, reported as the average of nine replicates:

| Release Timepoint | % Cumulative Gel Degradation (as measured by % zinc released into the saliva media) |
|---|---|
| 1 h | 0.82% ± 0.12% |
| 2 h | 1.51% ± 0.17% |
| 4 h | 2.71% ± 0.25% |
| 6 h | 4.00% ± 0.25% |
| 1 d | 8.15% ± 0.28% |
| 2 d | 14.01% ± 0.51% |
| 3 d | 19.98% ± 0.73% |
| 7 d | 31.13% ± 0.92% |
| 14 d | 39.77% ± 2.14% |
| 21 d | 46.43% ± 2.48% |
| 35 d | 54.03% ± 3.25% |
| 50 d | 62.72% ± 3.96% |

Example 6: Barrier Layer Protection Against Pathogens

The capability of polymer hydrogels according to the invention to provide barrier protection against bacteria is tested in a modified bacterial challenge assay. Sterilized hydroxyapatite disks and porcine buccal mucosa are exposed to 2 mL of sterile, filtered whole saliva pooled from two healthy volunteers for approximately 2 hours. Half of the substrates are then treated with the hydrogel Formula 1-9 (2 mL, 2 min) while the other half are dosed with phosphate-buffered saline (PBS, 1×) only (2 mL, 2 min) as control at room temperature. Samples are washed by dipping the substrates ten times in PBS (2 mL) at 37° C. Treated substrate samples are then inoculated with a saliva inoculum (1.5 mL/well, 2 mL whole saliva diluted in 40 mL McBain media with 80 μL Haemin, 1.6 μl Vitamin K, 400 μl Sucrose) and incubated at 37° C. for 24 hours. Samples are rinsed three times in cold sterile 0.25×TSB and analyzed for resistance to bacterial growth on each substrate via bacterial colony counts and reduction in ATP activity.

From visual inspection, it is apparent that the barrier formed by the oral hydrogel on mucosal tissue reduced bacterial re-colonization of the tissue by over 95% (at a $10^{-4}$ dilution). The bacterial barrier protection effect is also demonstrated by a reduction in ATP based activity for saliva inoculated substrates pretreated with the experimental hydrogel compared to the PBS control. The results are shown in the table below as the percent reduction for each sample versus the PBS control:

| Sample | Bacterial Viability (% reduction in ATP activity vs untreated control) |
|---|---|
| Formula 1-9 on HAP disk | 93% reduction |
| Formula 1-9 on mucosa | 95% reduction |

Example 7: Resistance to Bacterial Invasion

To assess bacterial resistance at different stages of gel degradation, samples used for evaluation are generated using the same degradation procedure detailed above in the saliva gel degradation experiments (Example 6). In the case of surface viability via ATP, 75 μL of an overnight grown bacteria culture composed of *Actinomyces viscosus* (ATCC #43146) & *Streptococcus oralis* (ATCC #35037) is placed on top of oral gel samples in the solidified state and incubated for 1 hour at 37° C. on an orbital shaker. Following the incubation period, analysis is done using the BacTiter-Glo Microbial Cell Viability Assay kit (Promega Ref #G8231) and reagents are added as per the manufacturer instructions. The ATP bioluminescence readout is used for analysis.

Three samples tested: (1) Formula 1-9, described above, having 0.075% CPC; (2) Formula 1-9 modified to have 0.04% CPC instead; and (3) a control having the formula according to 1-9 but with 000 CPC and 0%0 hyaluronic acid. The results are shown below as percent reduction in ATP bioluminescence versus the negative control (untreated).

| | Formula 1-9 (0.075% CPC) | | Formula 1-9 variant (0.04% CPC) | | Control | |
|---|---|---|---|---|---|---|
| | % Red. vs Unt. | St Dev. | % Red. vs Unt. | St Dev. | % Red. vs Unt. | St Dev. |
| Day 0 | 65% | 2% | 46% | 1% | −2% | 4% |
| Day 7 | 76% | 6% | 66% | 2% | 2% | 7% |
| Day 14 | 80% | 1% | 72% | 2% | 15% | 2% |
| Day 28 | 81% | 2% | 60% | 6% | −30% | 10% |

For viability via SIKT, the same gel degradation procedure as described above is used to treat an overnight culture of *Actinomyces viscosus* (ATCC #43146) and *Streptococcus oralis* (ATCC #35037). The cultures are treated with 100 μl of degraded oral gel for 30 seconds, after which the killing was stopped. Samples are then processed and the results are presented as a percentage of cells that are viable relative to a control sample treated with PBS alone (negative control).

| | Day 0 (n = 6) | Day 7 (n = 6) | Day 14 (n = 6) | Day 28 (n = 6) | Average (n = 24) |
|---|---|---|---|---|---|
| Negative Control | 100 | 100 | 100 | 100 | 100 |
| Ethanol | 16.8 | 14.5 | 14.7 | 19.0 | 16.3 |
| 1 * 182116 | 40.7 | 64.0 | 51.5 | 47.7 | 51.0 |
| 1 * 183748 | 57.5 | 97.0 | 92.5 | 55.2 | 75.5 |
| 1 * 82502 (Control) | 146.2 | 137.5 | 135.0 | 138.0 | 139.2 |

Example 8: Inhibition of Pro-Inflammatory Mediator PGE2 after LPS Induction

Hyaluronic acid has been shown to attenuate release of the pro-inflammatory cytokine IL-8 in cultured HEK-hTLR4 cells stimulated with bacterial lipopolysaccharide (LPS) in a dose-dependent fashion. This experiment is conducted to determine if a hydrogel comprising high-molecular weight hyaluronic acid can similarly inhibit release of the pro-inflammatory mediator PGE2 after stimulation of cells with LPS.

Mattek gingival tissues (n=3 per treatment group) are treated with 100 μL of the oral gel Formula 1-9 for 2.5 hours at 37° C. (with 5% CO2) in media containing 1 μg/mL *P. gigivalis* LPS (lipopolysaccharide). After 2.5 hours, tissues are washed with PBS (phosphate buffered saline), returned to the stimulated media, and incubated overnight. After overnight incubation, the tissue supernatant are collected and analyzed for PGE2 concentration. The results are shown in the table below:

| | PGE2 (pg/mL) | % reduction compared to medium + P. g. LPS |
|---|---|---|
| Medium + P. g. LPS | 1561.6 | |
| Placebo + P. g. LPS | 1257.3 | 19.5% |
| formula + P. g. LPS | 1096.5 | 29.7% |

Example 9: Maintenance of Gingival Tissue Viability

Tissue viability was tested by the MTT assay on tissue treated with the formula hydrogels. Mattek gingival tissues (n=3 per treatment group) are treated with 100 μL of the oral gel Formula 1-9 (2× dilution) for 2.5 hours at 37° C. (with 5% CO2) in media. After 2.5 hours, the tissues were washed with PBS. Non-stimulated tissues are incubated with 600 μl of 1 mg/ml of MTT solution (3-(4,5-dimethythiazol-2-yl)-2,5-diphenyltetrazolium bromide, or MTT) for 3 hours, then immersed into 1 mL of extractant solution (0.04N HCl in isopropyl alcohol) for 2-hours in the dark on a shaker to release the MTT to measure viability. The optical density of the extracted sample was measured at 570 nm and percent viability versus the negative control is calculated.

| | Tissue Viability (% visible in comparison vs negative control) |
|---|---|
| Placebo | 83.7% |
| Oral gel Formula 1-9 | 87.4% |

Example 10: Formula Optimization

A design of experiments is performed with the following variables: pH from 6 to 9; CPC concentration from 0 to 0.075%; and hyaluronic acid concentration from 0 to 0.8% (370 kDa). Rheological profiles, formula stability against sedimentation, healing (scratch assays), cytotoxicity, and micro robustness as a function of temperature are determined on the selected test formulas to further optimize properties for maximum therapeutic potential.

For the scratch assay, $5\times10^4$ HaCaT (P4) cells/well are seeded in 48-well plates. The cells are cultured 37° C. with 5% $CO_2$ for 1 to 2 days. Serial dilutions of formulas 12-1 through 12-13 are prepared in DMEM complete medium. A scratch was made across the center of the cells and images (T0) were acquired. Medium containing the formulas was added to the cells and the cultures were incubated at 37° C. with 5% $CO_2$ for 7 hours upon which images (T7) are repeated. The percent migration of the cell from T0 to T7 was calculated using Image J software.

For the cytotoxicity assays, $0.5\times10^4$ HaCaT (P4) cells/well are seeded in 96-well plates. The cells are cultured at 37° C. with 5% $CO_2$ overnight. Formulas 12-1 through 12-13 are pre-chilled at 4° C. for 2 hours. Serial dilutions of the formulas in DMEM complete medium are prepared. Medium containing the formulas is added to cells (duplicates for each treatment). Cells are cultured at 37° C. with 5% $CO_2$ for 24 hours. An Alamar blue assay is performed to determine viability.

For the microrobustness assay, a microrobustness index (MRI) value is calculated. The MRI compares the microrobustness of a new formula to an established category standard. This provides an assessment of a formula's ability to withstand an incidental microbiological insult, both during manufacturing and during consumer use. The Microrobustness Test (MRT) is used to generate the raw data point, an area under the curve (AUC) value. The MRT measures the rate of kill of a specified quantity of microbial inoculum—the less microbial growth present, the higher is the sample's resistance to microbial insult.

Standard industry procedures are used for the MRT. Briefly, a mixed bacterial culture including common oral species is grown, and then samples of each test material are inoculated with the culture, incubated briefly (0-2 hours), and then each mixture is plated onto sterile agar plates at multiple dilutions ($10^{-1}$ to $10^{-4}$). The plates are incubated for 48 hours, and then colony counts are performed. The log reduction in CFUs (colony forming units) is calculated at each time point versus the inoculum pool, and from this data the AUC is calculated. The MRI is then calculated as the ratio of the AUC of the test formula over the AUC of the reference standard. Alternatively, or in addition, the normalized (NAUC) value can be calculated which is the ratio of AUC of the test formula over the AUC of the standard, times one hundred.

The following formulas are tested (all values are in weight %; F127 is Pluronic F-127; 971P is Carbopol 971P; EG312 is ExpertGel312; all formulas are Q.S. water, ~85 wt %):

| | | | | | DOE Variables | | |
|---|---|---|---|---|---|---|---|
| Formula | F127 | 971P | EG312 | ZnO | CPC | pH | HA |
| 12-1 | 5 | 0.3 | 10 | 0.5 | 0.075 | 9 | 0.4 |
| 12-2 | 5 | 0.3 | 10 | 0.5 | 0 | 9 | 0.8 |
| 12-3 | 5 | 0.3 | 10 | 0.5 | 0 | 6 | 0.8 |
| 12-4 | 5 | 0.3 | 10 | 0.5 | 0 | 9 | 0 |
| 12-5 | 5 | 0.3 | 10 | 0.5 | 0.0375 | 6 | 0 |
| 12-6 | 5 | 0.3 | 10 | 0.5 | 0.075 | 9 | 0 |
| 12-7 | 5 | 0.3 | 10 | 0.5 | 0.075 | 6 | 0 |
| 12-8 | 5 | 0.3 | 10 | 0.5 | 0.075 | 6 | 0.8 |
| 12-9 | 5 | 0.3 | 10 | 0.5 | 0.0375 | 9 | 0.8 |
| 12-10 | 5 | 0.3 | 10 | 0.5 | 0.0375 | 7.5 | 0.4 |
| 12-11 | 5 | 0.3 | 10 | 0.5 | 0.075 | 7.5 | 0.8 |
| 12-12 | 5 | 0.3 | 10 | 0.5 | 0 | 7.5 | 0 |
| 12-13 | 5 | 0.3 | 10 | 0.5 | 0 | 6 | 0.4 |

A summary of the experimental outcomes from all studies are shown below. NAUC and MRI are two different methodologies for gauging microbial stability. MIC20 is an indication of cytotoxicity. The scratch test is used to gauge healing. Lumisizer AUC is an indication of sedimentation. G' is measured at 25° C. and at 37° C., and the ratio between them indicates the thermal response of the gel:

| Formula | MRI | MIC20 | Scratch (1:2000) | Lumisizer AUC | G' 37° C./ G' 25° C. | G' 25° C. (Pa) | G' 37° C. (Pa) | Yield Stress (Pa) | Gel Time (s) | Visc Max (Pa*s) |
|---|---|---|---|---|---|---|---|---|---|---|
| 12-1 | 0.78 | 0.16% | 92% | 1.96 | 350 | 10.59 | 3709 | 250 | 75 | 2,280 |
| 12-2 | 0 | 0.20% | 90% | 2.90 | 341 | 8.86 | 3025 | 210 | 87 | 1,765 |
| 12-3 | 0.12 | 0.25% | 88% | 24.27 | 369 | 7.47 | 2754 | 220 | 106 | 1,460 |
| 12-4 | 0.12 | 0.22% | 83% | 13.96 | 6376 | 0.45 | 2869 | 180 | 110 | 1,530 |
| 12-5 | 0.29 | 0.28% | 64% | 87.89 | 618 | 4.48 | 2768 | 180 | 110 | 1,790 |
| 12-6 | 1.63 | 0.13% | 63% | 14.27 | 13375 | 0.16 | 2140 | 220 | >300 | 1,200 |
| 12-7 | 0.35 | 0.10% | 71% | 89.17 | 558 | 3.73 | 2082 | 220 | 225 | 1,473 |
| 12-8 | 0.4 | 0.04% | 72% | 9.21 | 299 | 8.89 | 2657 | 230 | 108 | 1,500 |
| 12-9 | 0.83 | 0.13% | 92% | 8.30 | 123 | 30.75 | 3787 | 370 | 71 | 2,827 |
| 12-10 | 0.22 | 0.11% | 79% | 2.30 | 529 | 5.25 | 2775 | 220 | 100 | 1,620 |
| 12-11 | 0.26 | 0.09% | 67% | 2.48 | 296 | 13.89 | 4107 | 250 | 72 | 2,540 |
| 12-12 | 0 | 0.40% | 85% | 30.94 | 13129 | 0.07 | 919 | 250 | >300 | 660 |
| 12-13 | 0 | 0.20% | 61% | 78.95 | 501 | 4.61 | 2309 | 220 | 172 | 1,390 |

The data suggests an intricate interplay between the amount and type of poloxamers used (linear, crosslinked), the hyaluronic acid, and the carbomer, which permits optimization of the thermosensitive aspects of the formula (flowable fluid at room temperature, but elastic gel at oral temperature) while maximizing the potential benefits of the formulated system components including, mucoadhesion, anti-inflammatory activity and enhanced healing.

Example 11: Development of Poloxamer/Polyethylene Glycol Hydrogels

Rheological profiles (gelation properties) as a function of temperature were completed on a variety of hydrogel prototypes, demonstrating that a distinct combination of the different polymers is required to achieve the desired viscoelastic, thermosensitive profile (flowable, low viscosity at 25° C. and elastic gel at 37° C.). This formulation is unique amongst other systems in that both linear and crosslinked poloxamer are included in the vehicle, resulting in enhanced gel strength, carbomer is included for mucoadhesion, and high molecular weight hyaluronic acid (400 kDa-1 MDa) is utilized for mucoadhesion, anti-inflammatory, and healing benefits.

33 Test compositions are prepared which combine varying amounts of poloxamer 407, ExpertGel312, ExpertGel412, and polyethylene glycols of 6000, 8000, and 10,000 Da average molecular weight. Observations of gel morphology were made at 25° C. and 37° C. Evaluations of viscosity, gelation time and dissolution time in artificial saliva are made.

It is found that generally at least 14% by weight of gelling agents is necessary to provide gel formation at 37° C. The inclusion of Expert Gel 312 and Expert Gel 412 are shown to positively drive the yield stress of the formula, an important characteristic for the gel maintaining structure at 37° C. Expert Gel 312 is surprisingly found to promote the thermosensitive properties of poloxamer 407 in mixed formulations (e.g., with >19% gel, maintaining a viscous, but flowable liquid at 25° C. and gelation at 37° C.). Poloxamer 407 is found to drive a positive effect on the elasticity (G'/G") of the final formula gel.

Rheology parameters evaluated were yield stress, IVM, and elastic and viscous moduli. Yield stress (YS) characterizes how well the gel holds its form at 37° C. after completion of gelation. Instantaneous viscosity maximum (IVM) is an alternative characteristic of this same property. Elastic modulus (G') and viscous modulus (G") and their ratio (G'/G") are also assessed at 37° C.

Tested compositions are then evaluated for gelation was measured by two different means. An approximate gauge for gelation was measured by inversion of a droplet of material at a 45-degree angle and 90-degree angle after incubation at 37 C. Sample gelation was quantified by the amount of time that it took the fluid to gel and remain adhered to the slide in those positions. Samples were then classified on a scale of 1-4 (with 4 relating to samples with the shortest gelation time). Gelation time is also determined by heating a sample of the liquid as fast as possible from 4° C. to 37° C. on the rheometer. As a practical matter, this heating took an average of 20 seconds, so samples which gelled before 37° C. was reached are recorded as having a gelation time of 0 seconds. Three compositions (No. 7, 24 and 23) are found to have the most favorable gelation time.

Dissolution rate is evaluated using 0.7 g of gel suspended in artificial saliva under constant oscillation at 37° C. Sample observations are acquired every 30 minutes for the first seven hours upon which samples that still had visible gel were allowed to react overnight. Dissolution corresponded to completed visual absence of any solid or gel (complete dispersion in the saliva diluent. Samples that did not form gels at 37° C. were not tested. Samples ranged in dissolution time from 1 hour to 20 hours. For the applications described herein throughout, longer dissolution times are preferred in order to provide for sustained release of active ingredients entrained in the gel. Six compositions are found to have the most favorable dissolution times (No. 15, 28, 12, 29, 21, 16).

The compositions tested are shown in the following table (all table values are in weight %).

| F. # | PEG 6K | PEG 8K | PEG 10K | Total PEG | F127 | EG312 | EG412 | Total gelling agent | Water |
|---|---|---|---|---|---|---|---|---|---|
| 1 | 0 | 0.46 | 0.54 | 1 | 7.39 | 0 | 10 | 17.39 | 81.61 |
| 2 | 0.63 | 0.37 | 0 | 1 | 6.01 | 3.04 | 6.23 | 15.28 | 83.73 |
| 3 | 0 | 0.47 | 0.53 | 1 | 0 | 5.5 | 3.32 | 8.81 | 90.19 |
| 4 | 0 | 0 | 1 | 1 | 1.25 | 0 | 6.75 | 8 | 91 |
| 5 | 0.48 | 0 | 0 | 0.48 | 10.41 | 0 | 2.94 | 13.35 | 86.17 |
| 6 | 0 | 1 | 0 | 1 | 1.45 | 0 | 6.55 | 8 | 91 |

-continued

| F. # | PEG 6K | PEG 8K | PEG 10K | Total PEG | F127 | EG312 | EG412 | Total gelling agent | Water |
|---|---|---|---|---|---|---|---|---|---|
| 7 | 0.32 | 0.17 | 0.5 | 1 | 16.63 | 0 | 3.37 | 20 | 79 |
| 8 | 0.65 | 0.2 | 0 | 0.85 | 8.61 | 5.89 | 0 | 14.5 | 84.65 |
| 10 | 0 | 0.39 | 0.16 | 0.55 | 15.9 | 0.75 | 0 | 16.65 | 82.8 |
| 11 | 0.34 | 0 | 0.66 | 1 | 3.36 | 10 | 0 | 13.36 | 85.64 |
| 12 | 0.1 | 0 | 0 | 0.1 | 0 | 10 | 6.84 | 16.84 | 83.06 |
| 13 | 0 | 0.51 | 0 | 0.51 | 5.76 | 5.92 | 5.27 | 16.95 | 82.54 |
| 14 | 0.9 | 0 | 0 | 0.9 | 5.1 | 10 | 4.25 | 19.35 | 79.75 |
| 15 | 0.29 | 0.71 | 0 | 1 | 0 | 10 | 10 | 20 | 79 |
| 16 | 0.23 | 0 | 0 | 0.23 | 12.05 | 7.95 | 0 | 20 | 79.77 |
| 17 | 0.26 | 0.74 | 0 | 1 | 0.53 | 10 | 0 | 10.53 | 88.48 |
| 18 | 1 | 0 | 0 | 1 | 0 | 0 | 8 | 8 | 91 |
| 19 | 0.74 | 0 | 0 | 0.74 | 10 | 0 | 10 | 20 | 79.26 |
| 20 | 0 | 0.12 | 0.25 | 0.38 | 0 | 0 | 9.58 | 9.58 | 90.05 |
| 21 | 0 | 0.51 | 0 | 0.51 | 5.76 | 5.92 | 5.27 | 16.95 | 82.54 |
| 22 | 0.31 | 0 | 0.09 | 0.4 | 0 | 7.48 | 0.53 | 8 | 91.6 |
| 23 | 1 | 0 | 0 | 1 | 19.48 | 0 | 0 | 19.48 | 79.53 |
| 24 | 0 | 0 | 1 | 1 | 17.03 | 2.97 | 0 | 20 | 79 |
| 25 | 0 | 0 | 0.52 | 0.52 | 13.1 | 0 | 0 | 13.1 | 86.38 |
| 26 | 0 | 0 | 0.1 | 0.1 | 13 | 0 | 7 | 20 | 79.9 |
| 27 | 0.48 | 0 | 0 | 0.48 | 10.41 | 0 | 2.94 | 13.35 | 86.17 |
| 28 | 0.46 | 0 | 0.54 | 1 | 0 | 5.49 | 9.72 | 15.21 | 83.79 |
| 29 | 0 | 0 | 0.67 | 0.67 | 4.59 | 10 | 5.41 | 20 | 79.33 |
| 30 | 0 | 0.48 | 0 | 0.48 | 20 | 0 | 0 | 20 | 79.52 |
| 31 | 0.54 | 0.36 | 0.11 | 1 | 7.1 | 0.9 | 0 | 8 | 91 |
| 32 | 0 | 0.05 | 0.05 | 0.1 | 5.27 | 3.45 | 3.17 | 11.89 | 88.01 |
| 33 | 0 | 0.1 | 0 | 0.1 | 8 | 0 | 0 | 8 | 91.9 |
| 34 | 0 | 1 | 0 | 1 | 15.47 | 4.53 | 0 | 20 | 79 |

Based on the assessment of all of the above variables, the compositions tested could be ranked for the two primary parameters, gelation, and dissolution, as shown in the following table, along with rheology parameters (IVM, G' and G" are measured at 37° C.). In the second and third columns, gelation time (Gel.) and dissolution time (Diss.) are rated on a scale of 1-4, higher numbers being more favorable (faster gelation, slower dissolution), while in the ninth and tenth columns, actual gelation time and dissolution time are reported for certain samples:

| F. # | Gel. | Diss. | YS (Pa) | Inst. Visc. Max. (Pa*s) | G' | G" | G'/G" | Gel time (sec) | Diss. time (hr) | State at 25° C. | State at 37° C. |
|---|---|---|---|---|---|---|---|---|---|---|---|
| 1 | 2 | 2 | 715 | 11330 | 4900 | 2800 | 1.8 | 50 | 4.5 | viscous clear liquid | clear gel |
| 2 | 1 | 1 | 405 | 2979 | 1400 | 1400 | 1.0 | 100 | n/a | viscous clear liquid | extremely viscous liquid/gel |
| 3 | 1 | 1 | 155 | 117 | 1300 | 2300 | 0.6 | | n/a | clear liquid | viscous clear liquid |
| 4 | 1 | 1 | 115 | 178 | 170 | 150 | 1.1 | 76 | n/a | clear liquid | slightly hazy viscous liquid |
| 5 | 1 | 1 | 0 | 16 | 11 | 30 | 0.4 | | n/a | clear liquid | clear liquid |
| 6 | 1 | 1 | 45 | 111 | 75 | 75 | 1.0 | 82 | n/a | clear liquid | viscous, slightly hazy liquid |
| 7 | 4 | 2 | 196 | 18600 | 14000 | 1100 | 12.7 | 87 | 2 | clear gel | clear gel |
| 8 | 1 | 2 | 0 | 265 | 290 | 550 | 0.5 | | 1.5 | clear liquid | clear gel |
| 10 | 2 | 2 | 0 | 1223 | 0 | 0 | 0.0 | | 0.5 | slightly viscous, clear liquid | clear gel |
| 11 | 2 | 3 | 105 | 673 | 840 | 1400 | 0.6 | | 6.5 | viscous, clear liquid | extremely viscous, clear liquid |
| 12 | 3 | 4 | 765 | 9053 | 7000 | 3500 | 2.0 | 51 | 19 | extremely viscous, clear liquid | clear gel |

-continued

| F. # | Gel. | Diss. | YS (Pa) | Inst. Visc. Max. (Pa*s) | G' | G" | G'/G" | Gel time (sec) | Diss. time (hr) | State at 25° C. | State at 37° C. |
|---|---|---|---|---|---|---|---|---|---|---|---|
| 13 | 2 | 3 | 525 | 5725 | 2200 | 1300 | 1.7 | 52 | 7 | extremely viscous, clear liquid | clear gel |
| 14 | 2 | 3 | 985 | 18590 | 5800 | 2400 | 2.4 | 44 | 7+ to 15 | extremely viscous, clear liquid | clear gel |
| 15 | 3 | 4 | 1645 | 55320 | 11000 | 4000 | 2.8 | 39 | 20+ | extremely viscous (almost solid) clear liquid | clear gel |
| 16 | 3 | 4 | 115 | 4815 | 2500 | 1700 | 1.5 | 64 | 16 | slightly viscous, clear liquid | clear gel |
| 17 | 1 | 1 | 105 | 318 | 195 | 323 | 0.6 | | n/a | clear liquid | extremely viscous, clear liquid |
| 18 | 1 | 1 | 125 | 478 | 251 | 167 | 1.5 | 57 | n/a | clear liquid | extremely viscous, cloudy liquid |
| 19 | 2 | 3 | 1485 | 36440 | 11500 | 3000 | 3.8 | 39 | 6.5 | extremely viscous, clear liquid | clear gel |
| 20 | 1 | 1 | 225 | 662 | 465 | 300 | 1.6 | 52 | n/a | viscous, clear liquid | slightly hazy, extremely viscous liquid |
| 21 | 2 | 4 | 555 | 4458 | 3270 | 2070 | 1.6 | 54 | 16 | viscous, clear liquid | clear gel |
| 22 | 1 | 1 | 35 | 75 | 115 | 220 | 0.5 | | n/a | clear liquid | viscous, clear liquid |
| 23 | 4 | 2 | 100 | 16000 | 14700 | 690 | 21.3 | 0 | 1 | clear gel | clear gel |
| 24 | 4 | 2 | 267 | 64230 | 11200 | 860 | 13.0 | 28 | 2.5 | viscous, clear liquid | clear gel |
| 25 | 1 | 1 | 0 | 0 | 0 | 0 | | 97 | n/a | clear liquid | clear liquid |
| 26 | 3 | 2 | 315 | 23350 | 14700 | 2700 | 5.4 | 39 | 4.5 | clear gel | clear gel |
| 27 | 1 | 1 | 0 | 0 | 75 | 50 | | 92 | n/a | clear liquid | viscous, clear liquid |
| 28 | 3 | 4 | 575 | 9226 | 4700 | 2900 | 1.6 | 43 | 19 | Viscous (gel-like), clear liquid | clear gel |
| 29 | 3 | 4 | 1445 | 38280 | 13500 | 4400 | 3.1 | 34 | 16.5 | Viscous (gel-like), clear liquid | clear gel |
| 30 | 3 | 2 | 100 | 16000 | 17300 | 664 | 26.1 | 0 | 3 | clear gel | clear gel |
| 31 | 1 | 1 | 0 | 0 | 0 | 0 | | | n/a | clear liquid | clear liquid |
| 32 | 1 | 2 | 95 | 156 | 340 | 430 | 0.8 | | 3 | viscous, clear liquid | viscous, clear liquid |
| 33 | 1 | 1 | 0 | 0 | 0 | 0 | | | n/a | clear liquid | clear liquid |
| 34 | 3 | 2 | 883 | 690 | 804 | 0.9 | | | 2.5 | viscous, clear liquid | clear gel |

The results show that the most preferred compositions from this set of experiments is Formulas 12, 15, 16, 28 and 29. The results further support the following conclusions: (1) favorable viscosity characteristics are primarily driven by the presence and amount of the ExpertGel polymers (EG412 being more favorable than EG312), with a lesser effect from the Pluronic F-127; (2) favorable gelation characteristics are primarily driven by the presence and amount of Pluronic F-127, with a lesser and co-equal effect from the EG312 or EG412; (3) favorable dissolution characteristics are primarily driven by the presence and amount of the ExpertGel polymers (EG312 being more favorable than EG412), with a lesser effect from the Pluronic F-127.

Example 12: Hydrogel Based Oral Spray

An oral spray based on the preceding hydrogel technology is provided. This spray, while resembling the characteristics of normal saliva (texture, rheology), provides sustained ultra-oral lubrication and salivary stimulation. The following polymer compositions are formulated such as to transform from a liquid spray to a viscous gel resembling the properties of saliva at body temperature:

| Batch | F127 | EG312 | Sodium Saccharin | Carbopol 971P | Glycerin | NaOH 25% | 1 MDa HA | FD&C Blue 1 | CPC | Water |
|---|---|---|---|---|---|---|---|---|---|---|
| 12-1 | 0.45 | 4.45 | 0.2 | — | 10 | 0.2 | — | 0.002 | 0.015 | Q.S. |
| 12-2 | 0.45 | 4.45 | 0.2 | — | 10 | 0.2 | 0.2 | 0.002 | 0.015 | Q.S. |
| 12-3 | 0.45 | 4.45 | 0.2 | 0.30 | 10 | 0.4 | 0.2 | 0.002 | 0.015 | Q.S. |
| 12-4 | 0.45 | 4.45 | 0.2 | 0.15 | 10 | 0.2 | 0.2 | 0.002 | 0.015 | Q.S. |

The carbopol polymers built into the formulation promote gel adhesion to the oral mucosa. This mucoadhesion is expected to provide sustained lubrication, as well as the perception of slipperiness on oral tissues. other actives and excipients (arginine, xylitol, glycerin, zinc, etc) can be easily added to customize the consumer sensory experience or desired benefits of the base (ex. odor neutralization, anti-cavity).

Example 13: Low Water and Non-Aqueous Hydrogel Systems

While hydrogel compositions according to the present disclosure are primarily water and water/polyol-based liquids, there is also a need to formulate hydrogels in a way that permits protection and stability for water-sensitive actives. There is thus an interest in providing non-aqueous, preferably solid or semisolid, hydrogel compositions which will rehydrate on exposure to oral cavity saliva to form a liquid hydrogel that will then undergo the sol-gel transition as previously described. Several processes for attaining this goal are studied.

Freeze-Dried Hydrogels

To increase stability of water-sensitive actives, a freeze-dried hydrogel composition has been prepared. The process of freeze drying removes water via sublimation stabilizing the actives within the polymer matrix to create a precursor or concentrate. Reconstitution in room temperature or cold water (<15° C.) will dissolve the concentrate creating a diluted solution of active. Hydration in a minimal amount of warm water, saliva or artificial saliva (e.g., at 37° C.) will generate a gel for local application. The freeze-dried concentrate can be placed directly into the oral cavity directly with no exogenous water source necessary. Liquid hydrogel compositions according to the following formulas are prepared (amounts shown are in weight percent):

| F. # | F127 | EG312 | EG412 | PEG 8K | FD&C Blue 1 | Nicotinamide | Water |
|---|---|---|---|---|---|---|---|
| 13-1 | 20 | 0 | 0 | 0 | 1 | 0 | Q.S. (~79) |
| 13-2 | 20 | 0 | 0 | 0 | 0 | 1 | Q.S. (~79) |
| 13-3 | 20 | 0 | 0 | 0 | 0 | 0 | Q.S. (~80) |
| 13-4 | 0 | 10 | 10 | 0.7 | 0 | 0 | Q.S. (~79) |
| 13-5 | 5.75 | 5.9 | 5.25 | .5 | 0 | 0 | Q.S. (~83) |
| 13-6 | 0 | 10 | 10 | 0.7 | 1 | 0 | Q.S. (~78) |
| 13-7 | 5.75 | 5.9 | 5.25 | .5 | 1 | 0 | Q.S. (~82) |
| 13-8 | 0 | 10 | 10 | 0.7 | 0 | 1 | Q.S. (~79) |
| 13-9 | 5.75 | 5.9 | 5.25 | .5 | 0 | 1 | Q.S. (~82) |

The lyophilization removes all but trace amounts of water, resulting in approximately spherical or obolid products with a consistency similar to gum.

Low-Water Toothpaste Tablets

Compositions for thermogelling toothpaste tablets with rapid melt capabilities are detailed in the table below. These compositions deviate from other tablet compositions in that poloxamer 407 is the main ingredient, as opposed to salts like calcium carbonate, and other inorganics and fillers. The wafers are produced by freeze drying the initial gel formulation, generating a porous tablet structure. This composition and production process allows the delivery system to dissolve rapidly in aqueous media (water, saliva, mouthwash) and gel at body temperature. Moreover, water sensitive or oil-based actives can be encapsulated within the dry polymer matrix of the wafer for enhanced self stability. These include but are not limited to hydrogen peroxide, natural extracts, flavors, and oils, and readily oxidizable metals. Solid tablet hydrogel compositions according to the following formulas are prepared (amounts shown are in weight percent):

| F. # | Sorbitol 70% Aq. | F127 | CMC (Na) | Glycerin | NaF | Arginine | Silica | $CaCO_3$ | Water |
|---|---|---|---|---|---|---|---|---|---|
| 13-10 | 23 | 2 | 0.5 | | | | 8 | | Q.S. (~66) |
| 13-11 | 50 | 6 | 1.5 | | | | 24 | | Q.S. (~17) |
| 13-12 | 23 | 20 | 0.5 | | | | 8 | | Q.S. (~48) |
| 13-13 | 23 | 20 | 0.5 | 10 | | | 8 | | Q.S. (~38) |
| 13-14 | 23 | 6 | | | | | 24 | | Q.S. (~46) |
| 13-15 | 23 | 6 | | 10 | | | 24 | | Q.S. (~36) |
| 13-16 | 23 | 10 | | 10 | | | 24 | | Q.S. (~32) |
| 13-17 | 23 | 20 | | 10 | | | 24 | | Q.S. (~22) |
| 13-18 | 23 | 4 | | | | | 16 | | Q.S. (~56) |
| 13-19 | 23 | 4 | | 16 | | | 16 | | |
| 13-20 | 23 | 4 | | | | 16 | 16 | | |
| 13-21 | 23 | 4 | | | | 16 | | 16 | |
| 13-22 | 23 | 4 | | | | 3 | 50 | | |
| 13-23 | 23 | 6 | | | | 10 | 30 | | |
| 13-24 | 23 | 6 | | | | 10 | | 30 | |
| 13-25 | 23 | 6 | | | | 10 | 30 | | |
| 13-26 | 23 | 6 | | | | 10 | | 30 | |
| 13-27 | 23 | 2.5 | | | | | 8 | | |
| 13-28 | 23 | 2.5 | | | 0.3 | | 16 | | |
| 13-29 | 23 | 2.5 | | | 0.3 | 0.5 | 16 | | |
| 13-30 | 23 | 4 | | | | | 16 | | |
| 13-31 | 23 | 4 | | | 0.6 | | 32 | | |
| 13-32 | 23 | 4 | | | 0.6 | 3 | 32 | | |

On testing, these single-dose toothpaste tablets are found to rehydrate in the presence of a few drops of water to form a gel suitable for application to the teeth as a standard toothpaste. Dissolution is typically complete in about 6 seconds with gentle agitation. As shown, these formulas can successfully be prepared using common toothpaste ingredients, including sodium fluoride, silica abrasives, and arginine.

Anhydrous Hydrogel Pastes

To increase the stability of water sensitive actives, an anhydrous hydrogel precursor has been created. The precursor composition may consist of poloxamer 407 suspended in a non-aqueous water-miscible solvent, such as glycerin. The poloxamer may be prepared as a 25% solution in ethanol, blended with glycerin and sorbitol, and mixed at 37° C. to remove the ethanol. When immersed in warm artificial saliva the opaque paste transitions into a transparent hydrogel. As water exchanges with glycerin and solubilizes the poloxamer 407 and sorbitol, the polymer system hydrates faster than it dissolves, resulting in a thermosensitive, clear, gel of comparable volume within one minute. This system has the potential for the delivery of sensitive actives, such as, but not limited to hydrogen peroxide, natural extracts/oil, and readily oxidizable metals.

Several semi-solid (paste) hydrogel compositions are prepared for evaluation. Several combinations of polymers (including poloxamer 407, EG312, carrageenan, sodium alginate) and polyol carriers (glycerol, sorbitol, propylene glycol) are studied. It is found that pastes comprising poloxamer 407 in a glycerol or glycerol/ethanol carrier are most preferred as they provide the most stable gel, while propylene glycol-based gels are also suitable but dissolve faster after the completion of gelation. The use of ethanol as a co-carrier can assist solubilization of some ingredients, and optionally, most of the ethanol may be evaporated after formation of the paste. Exemplary compositions of anhydrous paste are as follows:

| F. # | Poloxamer 407 | Glycerin | Sorbitol | Ethanol |
|---|---|---|---|---|
| 13-33 | 1 | 1 | 0 | 3 |
| 13-34 | 1 | 1 | 0.22 | 3 |

Example 14: Hydrogel Comprising Low-Solubility Actives

Tetrahydrocurcumin is a highly insoluble drug. It has water solubility of about 6 μg/mL, and this has severely limited attempts to evaluate its in vitro or in vivo potency as a drug because of the difficulty of formulating compositions which can effectively deliver it to body tissues. It is thus a useful reference for compositions intended to deliver low-solubility active agents.

A range of hydrogel formulations are prepared in cold (4° C.) deionized water. Each cold formulation liquid is loaded with tetrahydrocurcumin (0.3 mg/mL of gel) via dispersion with a Speed Mixing apparatus (FlackTek, Inc). Samples are left to interact at 4° C. for 48 hours. Formulations are centrifuged at 10,000 rpm for 60 seconds to separate undissolved active. The saturation of active is determined via UV absorbance at 280 nm. With the hydrogel compositions investigated, the solubility of tetrahydrocurcumin is increased by up to 35 times that of its saturation point in water.

Liquid hydrogel compositions according to the following formulas are prepared (amounts shown are in weight percent) to evaluate tetrahydrocurcumin solubility:

| F. # | PEG-6000 | PEG-8000 | PEG-10000 | Pluronic F-127 | EG312 | EG412 | Water |
|---|---|---|---|---|---|---|---|
| 14-1 | 0.34 | | 0.66 | 3.36 | 10 | | Q.S. (~86) |
| 14-2 | 0.10 | | | | 10 | 6.8 | Q.S. (~83) |
| 14-3 | 0.90 | | | 5.10 | 10 | 4.25 | Q.S. (~80) |
| 14-4 | 0.29 | 0.71 | | | 10 | 10 | Q.S. (~79) |
| 14-5 | 0.23 | | | 12.05 | 8 | | Q.S. (~80) |
| 14-6 | 0.74 | | | 10.00 | | 10 | Q.S. (~79) |

-continued

| F. # | PEG-6000 | PEG-8000 | PEG-10000 | Pluronic F-127 | EG312 | EG412 | Water |
|---|---|---|---|---|---|---|---|
| 14-7 | | 0.51 | | 5.76 | 5.9 | 5.3 | Q.S. (~83) |
| 14-8 | 0.46 | | 0.54 | | 5.5 | 9.7 | Q.S. (~84) |
| 14-9 | | | 0.67 | 4.59 | 10 | 5.4 | Q.S. (~79) |
| 14-10 | | 0.48 | | 20.00 | | | Q.S. (~80) |
| 14-11 | 0.31 | | 0.62 | 3.96 | 6 | 10 | Q.S. (~79) |

Tetrahydrocurcumin is found to be soluble in the above tested gels at the following saturation concentrations:

| F. # | Solubility (mg/mL) |
|---|---|
| 14-1 | 0.107 |
| 14-2 | 0.159 |
| 14-3 | 0.127 |
| 14-4 | 0.111 |
| 14-5 | 0.168 |
| 14-6 | 0.193 |
| 14-7 | 0.134 |
| 14-8 | 0.086 |
| 14-9 | 0.208 |
| 14-10 | 0.161 |
| 14-11 | 0.188 |

The solubility of tetrahydrocurcumin is unexpectedly found to be significantly increased upon loading in hydrogel formulas in comparison to water. Tetrahydrocurcumin is found to have a solubility in the tested gels from 85 μg/mL to 236 μg/mL. It is found that the poloxamer-based components F-127, EG312 and EG412 are the primary drivers of tetrahydrocurcumin solubility.

Example 15: Further Formula Development

The following additional formulas 15-1, 15-2, and 15-3 are prepared, based on the leading formula 1-1

| Ingredient | Fm. 1-1 | Fm. 15-1 | Fm. 15-2 | Fm. 15-3 | Fm. 15-4 | Fm. 15-5 | Fm. 15-6 | Fm. 15-7 |
|---|---|---|---|---|---|---|---|---|
| Water | Q.S. (~84%) | Q.S. (~82%) | Q.S. (~83%) | Q.S. (~83%) | Q.S. (~80%) | Q.S. (~82%) | Q.S. (~81%) | Q.S. (~81%) |
| Chlorhexidine gluconate | 0 | 0 | 0 | 0 | 5 | 2.5 | 2.5 | 2.5 |
| Poloxamer 407 | 5 | 5 | 5 | 5 | 5 | 5 | 5 | 5 |
| Carbomer 971P | 0.3 | 0.3 | 0.3 | 0.3 | 0.3 | 0.3 | 0.3 | 0.3 |
| EG312 | 10 | 10 | 10 | 10 | 10 | 10 | 10 | 10 |
| Sodium Hyaluronate (high-MW) | 0.4 | 0.4 | 0.4 | 0.4 | 0 | 0 | 0.4 | 0.4 |
| CPC | 0.075 | 0.075 | 0.075 | 0.075 | 0.015 | 0.015 | 0.075 | 0.075 |
| Zinc Oxide | 0.5 | 0 | 0 | 0 | 0 | 0 | 0 | 0 |
| NaOH (50% Aq) | 0.15 | 0 | 0 | 0 | 0 | 0 | 0 | 0 |
| Sodium bicarbonate | 0 | 0.38 | 0.38 | 0.38 | 0 | 0 | 0.38 | 0 |
| Sodium carbonate | 0 | 0.36 | 0.36 | 0.36 | 0 | 0 | 0.36 | 0 |
| Cocamidopropyl betaine | 0 | 1.5 | 0 | 0 | 0 | 0 | 0 | 0 |
| p-Hydroxy-acetophenone | 0 | 0 | 0.12 | 0 | 0 | 0 | 0 | 0 |
| Eugenol | 0 | 0 | 0 | 0.3 | 0 | 0 | 0 | 0 |

Hyaluronic acid used in these formulations has a molecular weight of about 250-350 kDa. Viscosity related measurements are taken at 25° C. and 37° C., as described in Example 3 above. The following results are obtained:

| | 37° C. | | | | | 25° C. | | |
|---|---|---|---|---|---|---|---|---|
| Sample | Yield Stress (Pa) | ViscMax (Pa-s) | G' (Pa) | G" (Pa) | G'/G" | G' (Pa) | G" (Pa) | G'/G" |
| Formula 15-1 | 295 | 9812 | 6095 | 2378 | 2.6 | 108 | 505 | 0.21 |
| Formula 15-1 + mucin | 445 | 23050 | 5672 | 1092 | 5.2 | 2006 | 1945 | 1.02 |
| Formula 15-2 | 175 | 4355 | 4709 | 2584 | 1.8 | 15 | 150 | 0.1 |
| Formula 15-2 + mucin | 335 | 12770 | 5157 | 1311 | 3.9 | 915 | 1461 | 0.62 |
| Formula 15-3 | 375 | 8003 | 5320 | 2063 | 2.6 | 146 | 599 | 0.24 |
| Formula 15-3 + mucin | 354 | 31530 | 5731 | 995 | 5.8 | 2792 | 2078 | 1.34 |
| Formula 15-4 | 285 | 784 | 1381 | 2179 | 2179 | — | — | — |
| Formula 15-4 + mucin | 474 | 18730 | 7385 | 1860 | 1860 | — | — | — |
| Formula 15-5 | 265 | 1796 | 3053 | 3154 | 3154 | — | — | — |
| Formula 15-5 + mucin | 314 | 13100 | 6687 | 1898 | 1898 | — | — | — |

The results demonstrate that each of formulas 15-1, 15-2 and 15-3 are fluid at room temperature (a G'/G" ratio of less than 1 is a fluid), while after mixing with mucin at room temperature, or after warming to body temperature, these three compositions convert to a gel (G'/G" ratio>1). Similar results are obtained for formulas 15-4, 15-5 and 15-6 at 37° C., with results at room temperature expected to be correspondingly similar.

It is believed that cocamidopropylbetaine acts as stabilizer to improve the availability and efficacy of the cetylpyridinium chloride (CPC) antibacterial agent. Therefore, an additional comparison is performed using Formula 15-1 against the same formula having no cocamidopropylbetaine (having an additional 1.5 wt % water instead). Under accelerated aging conditions, it is found that the concentration of CPC is maintained at 100% for the CAPB-stabilized formulation, whereas without CAPB, the CPC recovery is reduced to 97%.

Example 16: Physical Stability of Chlorhexidine Formulations

It is observed that the chlorhexidine-containing compositions 15-4, 15-5, 15-6 and 15-7 are opaque white. This is believed to be due to the formation of insoluble chlorhexidine complexes within the hydrogel polymer matrix. As the polymer matrix includes large molecular weight anionic polymers, the precipitated chlorhexidine complexes become supported within the gel matrix and do not settle out under gravity. The gravitational stability of this opacity was confirmed by performing gravitational testing at 2300 ref (relative centrifugal force). for 36 hours on samples of formulations 15-4 and 15-5. Briefly, samples were loaded on a Lumisizer dispersion analyzer in cuvettes at 25° C. Aging was performed at 2300 rcf for 24 hours at 25° C. followed by an additional 12 hours at 10° C. Settling was assessed by light transmission through the sample integrated over the length of the sample. The results are shown in the table below:

| Sample | Time | Temperature | Integral Transmission |
|---|---|---|---|
| 15-4 | 0 hours | 25° C. | 10.7% |
| 15-4 | 25 hours | 25° C. | 7.4% |
| 15-4 | 36 hours | 10° C. | 8.5% |
| 15-5 | 0 hours | 25° C. | 10.2% |
| 15-5 | 24 hours | 25° C. | 8.3% |
| 15-5 | 36 hours | 10° C. | 13.5% |

The results show that opacity is maintained throughout the experiment for both formulations tested. This is evidence supporting the physical stability of the formulations against bulk precipitation, which could adversely affect delivery of active and thus efficacy. Since the CHX remains uniformly distributed, this is not a concern.

Example 17: Chemical Stability of Chlorhexidine Formulations

Chlorhexidine is known to undergo degradation to form para-chloroaniline (PCA), and it has been difficult to formulate chlorhexidine compositions to maximize chemical stability during storage or aging. Formulations 15-4, 15-5 and 15-6 were evaluated under accelerated aging conditions to determine whether the formulations of the present disclosure stabilize the chlorhexidine against degradation. Samples were maintained for 13 weeks at either 4° C. or 40° C., with samples taken for analysis at 4 weeks and 13 weeks. The results are shown in the following table, expressed as ppm PCA/% chlorhexidine:

| Time | Temperature | Fm. 15-4 | Fm. 15-5 | Fm. 15-6 (pH 9) | Fm. 15-6 (pH 6.5) |
|---|---|---|---|---|---|
| Initial | | 9.1 | 8.8 | 10.0 | 12.0 |
| 4 weeks | 4° C. | 8.9 | 11.2 | 10.4 | 10.4 |
| 13 weeks | 4° C. | 8.7 | 7.6 | 10.4 | 10.0 |
| 4 weeks | 40° C. | 11.0 | 10.8 | 13.2 | 12.4 |
| 13 weeks | 40° C. | 16.5 | 14.0 | 12.4 | 13.6 |

It is found that in some of the formulations investigated (e.g., formulation 15-6), the chlorhexidine undergoes negligible degradation during storage (PCA levels are essentially unchanged compared to initial formulation).

The invention claimed is:

1. A liquid thermosensitive hydrogel comprising:

(a) from about 0.1 to about 20 wt. % of a linear polyethylene glycol(PEG)/polypropylene glycol(PPG) triblock copolymer, (b) from about 1 to about 20 wt. % of a copolymer of (i) linear PEG/PPG triblock copolymer, and (ii) polypropylene glycol(PPG)-saturated methylene diphenyl diisocyanate(SMDI), and (c) an aqueous carrier.

2. The hydrogel of claim 1, wherein the hydrogel comprises the linear PEG/PPG triblock copolymer in an amount of 1 to 10 wt %.

3. The hydrogel of claim 1, wherein the hydrogel comprises the linear PEG/PPG triblock copolymer and PPG-SMDI copolymer in an amount of 5-15 wt %.

4. The hydrogel of claim 1, further comprising ethanol, glycerol, propylene glycol, sorbitol, xylitol, or mixtures thereof.

5. The hydrogel of claim 1, wherein the water is present in an amount of 50 to 90 wt. %.

6. The hydrogel of claim 1, wherein the hydrogel further comprises one or more of (d) a polyethylene glycol (PEG) polymer, (e) a polyacrylic acid or polyacrylate polymer, (f) hyaluronic acid or an alkali metal hyaluronate polymer having a molecular weight >100,000 Da, and (g) one or more active agents.

7. The hydrogel of claim 1, wherein the hydrogel further comprises a polyacrylic acid or polyacrylate polymer.

8. The hydrogel of claim 7, wherein the polyacrylic acid or polyacrylate polymer is a cross-linked polymer having a viscosity of 29,000 to 40,000 mPa-s.

9. The hydrogel of claim 7, wherein the hydrogel comprises the polyacrylic acid or polyacrylate polymer in an amount of 0.05 to 5 wt %.

10. The hydrogel of claim 1, wherein the hydrogel further comprises hyaluronic acid or an alkali metal hyaluronate polymer having a molecular weight >100,000 Da.

11. They hydrogel of claim 10, wherein the hyaluronic acid or alkali metal hyaluronate polymer has an average molecular weight of 200,000 to 1,500,000 Da.

12. The hydrogel of claim 11, wherein the hydrogel comprises the hyaluronic acid or alkali metal hyaluronate polymer in an amount of 0.01 to 10 wt %.

13. The hydrogel of claim 1, wherein the hydrogel further comprises an active agent selected from: zinc oxide, cetylpyridinium chloride, chlorhexidine gluconate, eugenol and a combination of two or more thereof.

14. The hydrogel of claim 1, wherein the hydrogel does not comprise a polyethylene glycol polymer.

15. A kit comprising a hydrogel according to claim 1 and an oral administration device.

16. A method of treating or preventing a disease of the oral cavity comprising administering to the oral cavity a hydrogel according to claim 1, wherein the disease of the oral cavity is selected from: periodontal disease, dental caries, dental hypersensitivity, halitosis, and oral infections.

17. The method according to claim 16, wherein the hydrogel is administered by injection into the periodontal cavity, the periodontal pocket, or the gingival pocket.

* * * * *